(12) United States Patent
Muratani et al.

(10) Patent No.: US 9,506,110 B2
(45) Date of Patent: Nov. 29, 2016

(54) PROCESSING OF AMPLIFIED DNA FRAGMENTS FOR SEQUENCING

(75) Inventors: Masafumi Muratani, Singapore (SG); Huck Hui Ng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 154 days.

(21) Appl. No.: 13/515,953

(22) PCT Filed: Dec. 15, 2010

(86) PCT No.: PCT/SG2010/000467
§ 371 (c)(1),
(2), (4) Date: Jun. 14, 2012

(87) PCT Pub. No.: WO2011/075083
PCT Pub. Date: Jun. 23, 2011

(65) Prior Publication Data
US 2012/0252702 A1    Oct. 4, 2012

(30) Foreign Application Priority Data

Dec. 15, 2009   (SG) .................................. 200908342

(51) Int. Cl.
*C12Q 1/68*         (2006.01)
*C12P 19/34*        (2006.01)

(52) U.S. Cl.
CPC .................................. *C12Q 1/6846* (2013.01)

(58) Field of Classification Search
None
See application file for complete search history.

(56) References Cited

U.S. PATENT DOCUMENTS

| 6,413,758 | B1 * | 7/2002 | Xu et al. ........................ 435/199 |
| 7,135,310 | B2 * | 11/2006 | Bradbury et al. ............ 435/91.1 |
| 2007/0196842 | A1 * | 8/2007 | Dhallan ............................. 435/6 |

FOREIGN PATENT DOCUMENTS

| WO | WO-2007/149789 A2 | 12/2007 |
| WO | WO-2011/075083 A1 | 6/2011 |

OTHER PUBLICATIONS

Rodrigue et al., "Whole Genome Amplification and De novo Assembly of Single Bacterial Cells", PLoS One, vol. 4, Iss. 9 p. 1-10 (2009).*
New England BioLabs, Inc., BpmI restriction enzyme product sheet (accessed at http://www.neb.com/nebecomm/products_intl/productr0565.asp on Nov. 15, 2012).*
Lister et al., "Finding the fifth base: Genome-wide sequencing of cytosine methylation," Genome Research, 2009, vol. 19, pp. 959-966.*
International Search Report and Written Opinion for PCT/SG2010/000467 mailed Feb. 17, 2011.
International Preliminary Report on Patentability for PCT/SG2010/000467 mailed Jun. 28, 2012.
Laken et al., Genotyping by mass spectrometric analysis of short DNA fragments. Nat Biotechnol. Dec. 1998;16(13):1352-6.
Mantovani et al., A high throughput method for genome-wide analysis of retroviral integration. Nucleic Acids Res. 2006;34(19):e134. 6 pages. Epub Oct. 5, 2006.
Sorber et al., The long march: a sample preparation technique that enhances contig length and coverage by high-throughput short-read sequencing. PLoS One. 2008;3(10):e3495. 9 pages. doi: 10.1371/journal.pone.0003495. Epub Oct. 22, 2008.

* cited by examiner

*Primary Examiner* — Young J Kim
(74) *Attorney, Agent, or Firm* — Wolf, Greenfield & Sacks, P.C.

(57) ABSTRACT

A processing method to trim ends of DNA fragments, exposing the internal DNA part to give original DNA sequence information enabling application of next generation sequencing for DNA samples to be amplified by DOP-PCR or other primer dependent amplification methods. Specifically, nucleic acids are amplified using primers comprising a recognition site for a restriction enzyme, for example BpmI or MmeI. Primer sequences are removed by cleavage with the restriction enzyme.

8 Claims, 34 Drawing Sheets

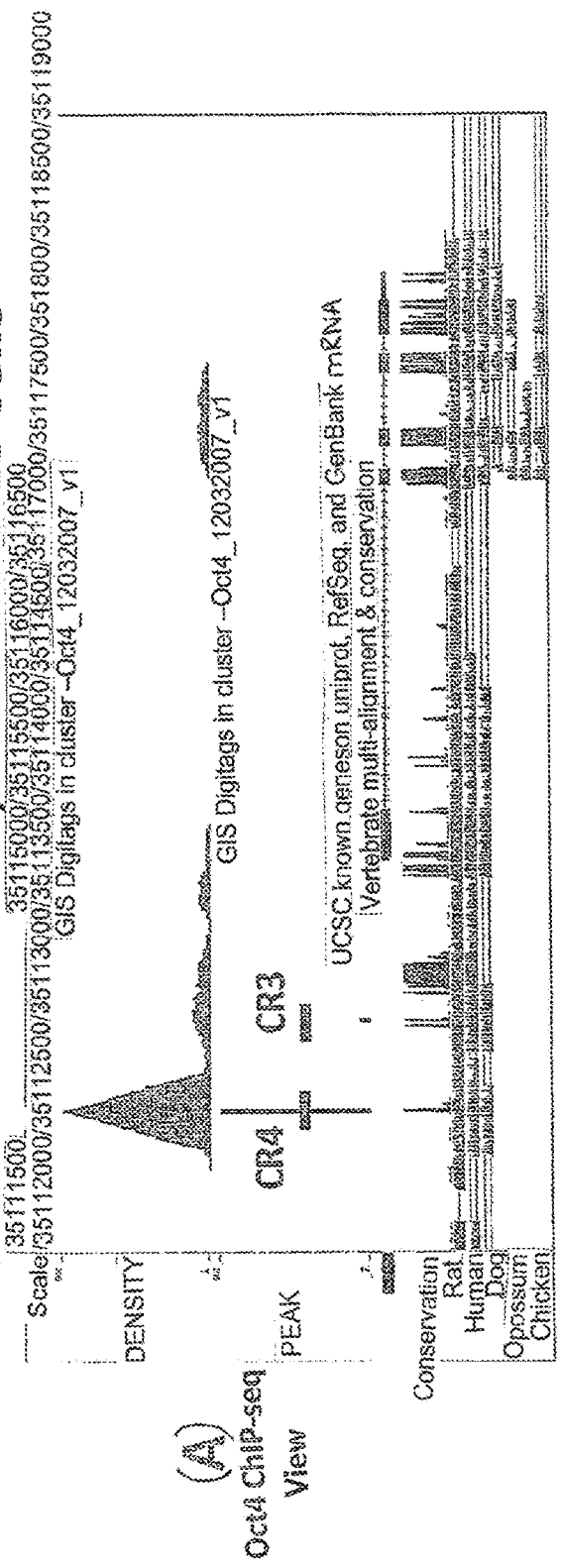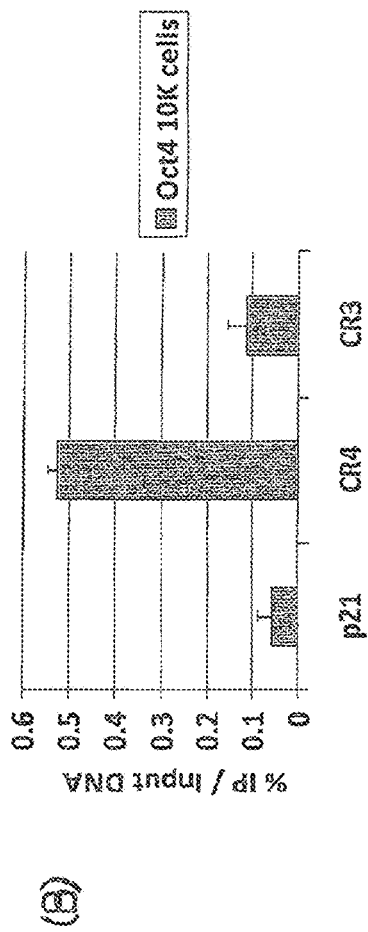
Figure 6

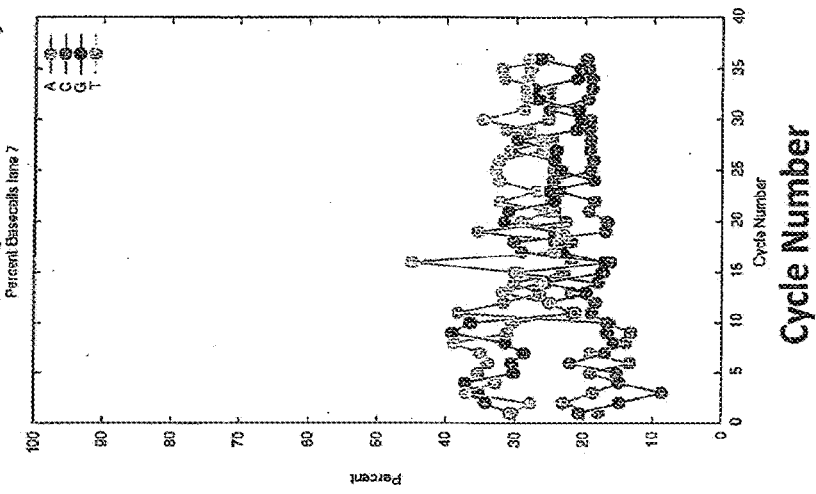
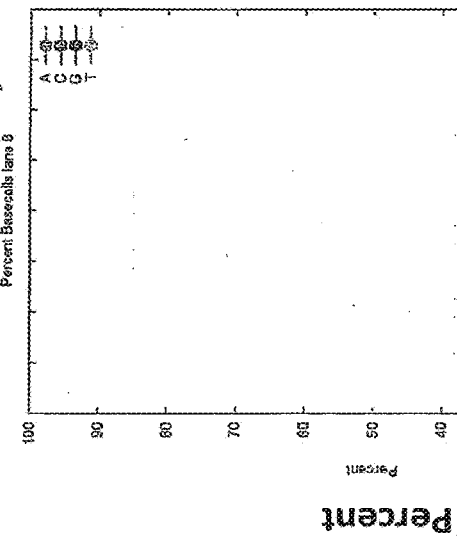
Figure 17

Topo-Cloning and Sequencing of Sigma-WGA Fragment

Bpm I Digest ▽  
Sigma Primer    ?     Perfect Match to the Genome

TGTGTTGGGTGTGTGTTTGGTGGTTTGGGTACACGCCTTTAATCCAGCACTTGGGA
GGCAGAGACAGGCGGATTTCTGAGTTCAAGGCCAGCCTGGTCTACAAAAGTGA
GTTCCAGGACAGCCAGAGCTATACAGAGAAACTGCCTCAAAAAAACAAAA
ACAAAACAAAACAAAACAAAACAAAACAAAACGCCTACAACTCTTGTAAAGGA
CTTGAGTTTGGTCCCAGCATCAACATGGCTATCAATGTTGTAACCAACCCC
CACAACCCCAAACACACCCAACACAA (11~253/260 matched to genome)

Figure 18     30-cycle WGA fragments

Topo-Cloning and Sequencing of Sigma-WGA Fragment

Sigma Primer | Bpm I Digest | ? | Perfect Match to the Genome

TGTGTTGGGTGTGTTTGGTGTGGTTTGGGTACACGGCCTTTAATCCCAGCACTTGGGA
GGCAGAGACAGGGGGATTTCTGAGTTCAAGGCCAGCCTGGTCTACAAAAGTGA
GTTCCAGGACAGCCAGAGAGCTATACAGAGAAAACAAAAACTCTGCCTCAAAAACAAAA
ACAAAACAAAACAAAACAAAAACAAAAACAAAAACGCCTACAACTCTTGTAAAGGA
CTTGAGTTTGGTCCCCAGCATCAACATCGGCTATCAATGCTTGTAACACCAACCCC
CACAACCCCAAACACACCCAACACACAA (11~253/260 matched to genome)

▽

TGTGTTGGGTGTGTTTGGTGTGGTGTGGAAAATTTAGAAAATGTCCACTGTAGG
ACGTGGAATATGGCAAGAAAACTGAAAATCATGGAAAATGAGAAACATCCACTT
GACGACTTGAAAAATGACGAAATCACTAAAAACGTGAAAAATGAGAAATGCC
CACTAAAGGACCTGGGATATGGCGAGTAAACTGAAAATCACGGAAAATGAGAA
ATACACACTTTAGGACGTGAAATATGGCGAGGAAAACTGAAAAGGTGGAAAAT
ATAGAAAATGTCCACGTAGGACGTGGAATATGGCAAGAAAACCAAAAACCAAAC
ACACCCAACACACAA (9~298/298 matched to genome)

30-cycle WGA fragments

Figure 19

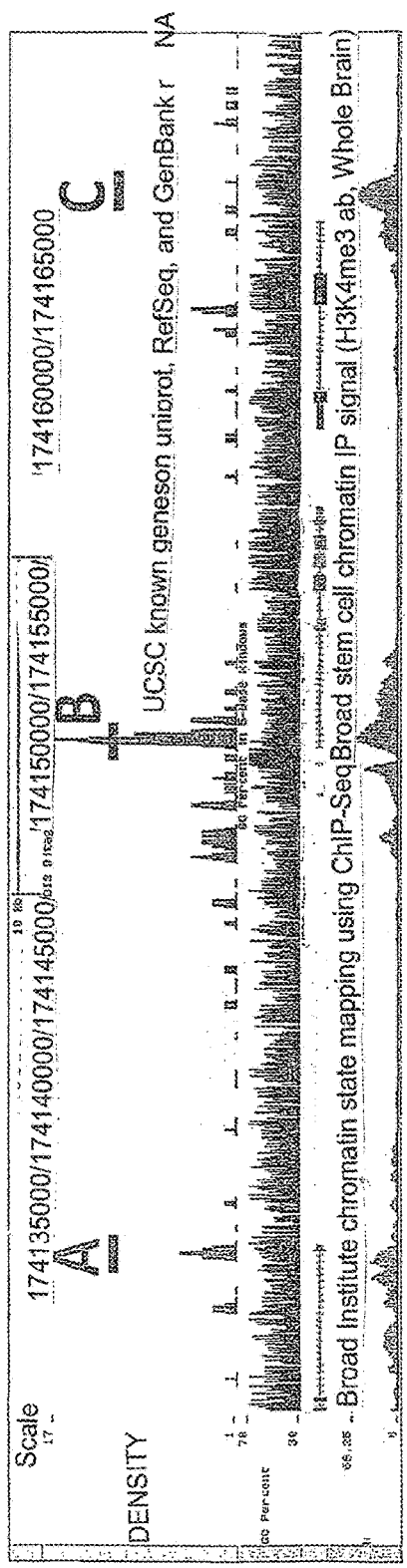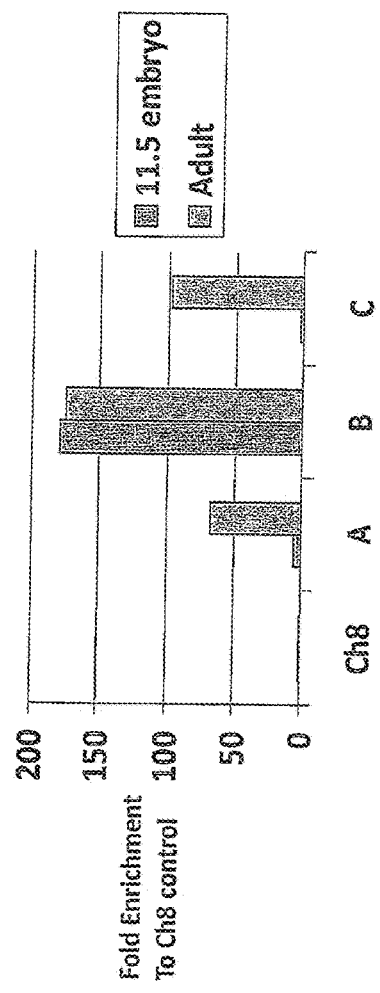
Figure 32 ize application No. 200908342-

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: restriction enzyme recogintion site
<220> FEATURE:
<221> NAME/KEY: misc_feature
<222> LOCATION: (1)..(14)
<223> OTHER INFORMATION: n is a, c, g, t or u

<400> SEQUENCE: 1
nnnnnnnnnn nnnngacctc                                               20

<210> SEQ ID NO 2
<211> LENGTH: 22
<212> TYPE: DNA
<213> ORGANISM: Bacillus pumilus
<220> FEATURE:
<221> NAME/KEY: misc_feature
<222> LOCATION: (7)..(22)
<223> OTHER INFORMATION: n is a, c, g, t or u

<400> SEQUENCE: 2
ctggagnnnn nnnnnnnnnn nn                                            22
```

PROCESSING OF AMPLIFIED DNA FRAGMENTS FOR SEQUENCING

CROSS-REFERENCE TO RELATED APPLICATION

This application is a U.S. National Stage application based on International Application No. PCT/SG2010/000467, filed 15 Dec. 2010, which claims benefit of, and priority from, Singapore patent application No. 200908342-9, filed on 15 Dec. 2009, the contents of each of which are hereby incorporated herein by reference.

FIELD

DNA amplification and or processing used for genomic sequencing, epigenetics and or Transcriptome analysis.

BACKGROUND

Massively parallel sequencing and next generation sequencing platforms are rapidly transforming data collection and analysis in genome, epigenome and transcriptome research. Most of these sequencing technologies read relatively short oligonucleotide sequences from the ends of DNA fragments. For examples, sequencers from Illumina and Applied Biosystems provide reliable reads up to about 50 bases, and Paired-End-Tag (PET) method reads only 20 or 27 bases. This is due to the DNA processing enzymes MmeI or EcoP15I used to generate the tags.

Efficiency of ChIP assay is generally low with only two copies of targets per cell usually possible. Transcription factor binding may not be stable at such low values. 1%=~20 molecules/locus in final IP sample.

Degenerate Oligonucleotide Primed-Polymerase Chain Reaction (DOP-PCR) is a robust method to amplify trace amount of DNA for various downstream applications such as sequencing and genotyping. However, this method relies on addition of sequences (>18 bases) to the ends of original DNA fragments—making it unfavorable for next generation sequencing as they produce only short sequence reads. DOP-PCR utilise 3' degenerate sequence part of primers for initial library synthesis and fixed 5' sequence for following exponential amplification by PCR (see FIG. 8). DOP-PCR has several problems:
  (i) Fixed 5' primer sequence at the ends of amplified fragments. Every amplification product has primer sequence: at both ends as a result of PCR amplification.
  (ii) Mutations introduced by degenerate priming and PCR amplification. Non-perfect annealing of degenerate oligo primers during library synthesis and mispriming events during PCR cause mutation and addition of sequences at the ends of amplified fragments.

SUMMARY

The invention seeks to ameliorate some of the problems of the prior art.

Accordingly a first aspect of the invention comprises a method of trimming nucleic acid fragments for sequencing comprising the steps of:
  (i) Amplifying a nucleic acid fragment with a primer comprising a target primer sequence and a recognition site for a restriction enzyme;
  (ii) Digesting the amplified nucleic acid fragment with a restriction enzyme to remove the primer sequence thereby exposing the target sequence.

A further aspect of the invention comprises a primer sequence comprising a target primer sequence and a recognition site for a restriction enzyme.

A further aspect of the invention comprises a sample preparation kit comprising a primer sequence comprising a target primer sequence and a recognition site for a restriction enzyme of the invention and a restriction enzyme.

BRIEF DESCRIPTION OF THE DRAWINGS

Preferred embodiments of the invention will be described with reference to the following drawings of which:
FIG. 6: Oct4 ChIP with 10,000 mouse ES cells
FIG. 17: WGA Library Fragments are T/G rich at 5' end
FIG. 18: Topo-Cloning and Sequencing of Sigma-WGA Fragment
FIG. 19: Topo-Cloning and Sequencing of Sigma-WGA Fragment
FIG. 32: Verification of ChIP-seq Results by Real-Time PCR

DETAILED DESCRIPTION OF PREFERRED EMBODIMENTS

Figure 1:
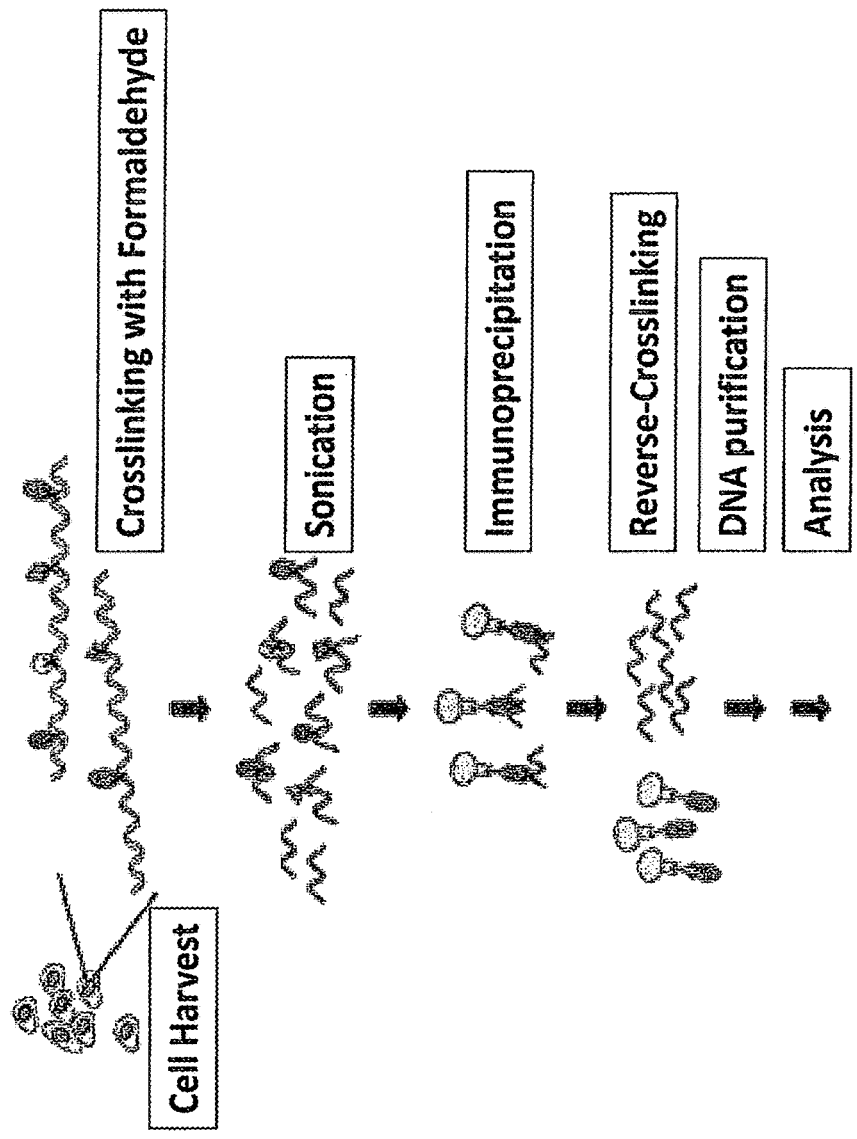
FIG. 1: Chromatin Immunoprecipitation Assay

To solve this problem, we developed a processing method to trim ends of DNA fragments. Thus exposing the internal DNA part to give original DNA sequence information (FIGS. 13, 14 and 20) enabling application of next generation sequencing for DNA samples to be amplified by DOP-PCR or other primer-dependent amplification methods.

Accordingly a first aspect of the invention comprises a method of trimming nucleic acid fragments for sequencing comprising the steps of:
(i) Amplifying a nucleic acid fragment with a primer comprising a target primer sequence and a recognition site for a restriction enzyme;
(ii) Digesting the amplified nucleic acid fragment with a restriction enzyme to remove the primer sequence thereby exposing the target sequence.

A further aspect of the invention comprises a primer sequence comprising a target primer sequence and a recognition site for a restriction enzyme.

A further aspect of the invention comprises a sample preparation kit comprising a primer sequence comprising a target primer sequence and a recognition site for a restriction enzyme of the invention and a restriction enzyme.

Preferably the method uses the restriction enzyme that cleaves the sequence outside of the recognition site. Such as a restriction enzyme selected from BpmI or MmeI or any other such restriction enzymes known in the art. There are many restriction enzymes that cut outside of recognition site, similar enzymes for example those in the product catalogue from New England Biolab contain more than 50 such enzymes, and there are more known in the art.

In a preferred embodiment the recognition site comprises SEQ ID NO.: 1 and the restriction enzyme comprises SEQ ID NO.:2.

The method may further comprise the step of digesting the amplified nucleic acid fragment with a restriction enzyme a second time or a plurality of times.

The method may further comprise the step of forming a nucleic acid library using whole genome amplification. In one embodiment the method may further comprise the step of computationally removing any bias in the nucleic acid library.

In a preferred embodiment the primer may be adapted to be cleaved by a restriction enzyme sequence outside of the recognition site.

In a preferred embodiment the recognition site comprises SEQ ID NO.: 1.

In a preferred embodiment the restriction enzyme of the kit cleaves the sequence outside of the recognition site. Such as a restriction enzyme selected from BpmI or MmeI or any other such restriction enzymes known in the art. There are many similar enzymes for example those in the product catalogue from New England Biolab contain more than 50 such enzymes, and there are more known in the art.

Preferably the restriction enzyme of the kit is selected from BpmI or MmeI. In one embodiment the recognition site of the kit comprises SEQ ID NO.: 1 and the restriction enzyme of the kit comprises SEQ ID NO.:2.

This is a method to trim ends of DNA fragments to expose the internal part of the DNA sequence. This method can be applied for manufacturing a DNA library amplified by DOP-PCR and other PCR-based amplification methods.

The method may use ChIP protocol for small-scale assay then Whole Genome Amplification for ChIP DNA followed by Processing WGA Library for Solexa sequencing DNA fragments are amplified with a primer. The primer contains the original PCR primer sequence such as a target primer of interest and a recognition site for a restriction enzyme that cleaves outside of the recognition site there are many restriction enzymes that cut outside of recognition site. The restriction enzyme preferably cleaves the amplified DNA fragments outside the recognition site such as BpmI and MmeI restriction enzymes that cleave outside of the recognition sequence. Following amplification, DNA fragments are digested with the restriction enzyme to remove the primer sequence used for amplification. Preferably the recognition site comprises SEQ ID NO. 1: 3' GAC-CTCNNNNNNNNNNNNNN 5'. Preferably the restriction enzyme sequence comprises SEQ ID NO. 2: 5' CTG-GAGNNNNNNNNNNNNNNNN 3'.

This DNA processing can be further followed by ligation of adaptor with restriction site and repeat of digestion if further trimming of amplified DNA fragment is required.

Figure 16:
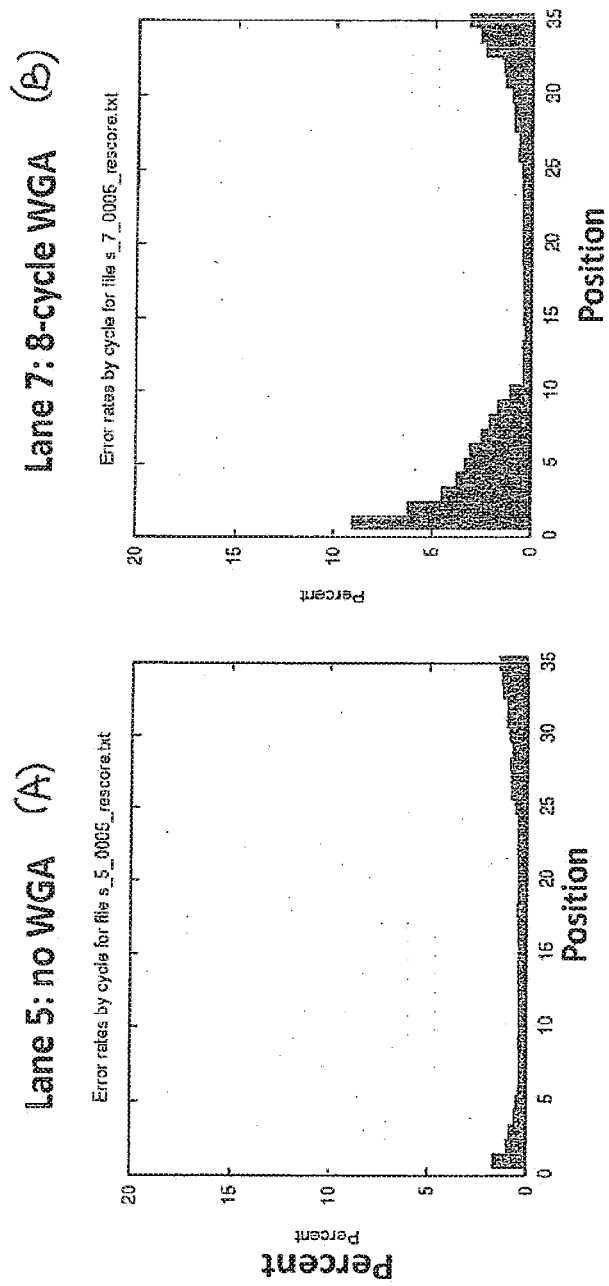
FIG. 16: Error Rates at 5' End
Figure 21:
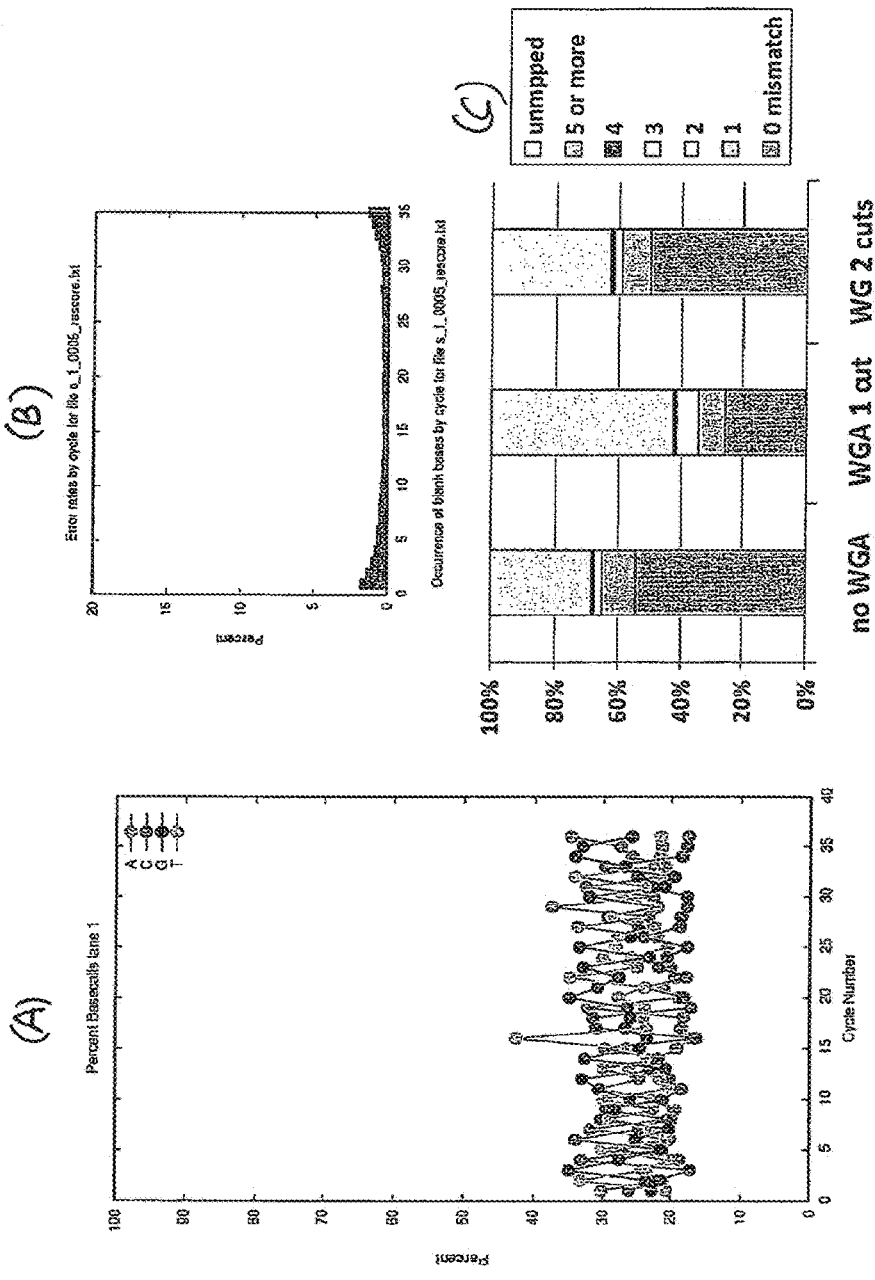
FIG. 21: Second Bpm I Digest Improved Mapping of WGA Library
Figure 22:
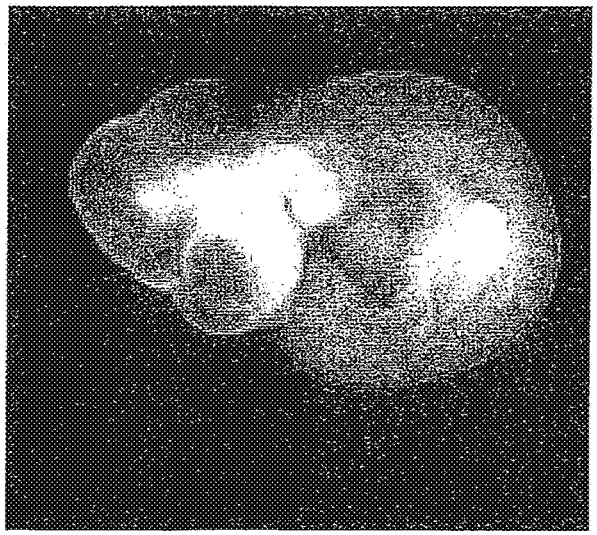
FIG. 22: ChIP with embryo tissue
Figure 23:
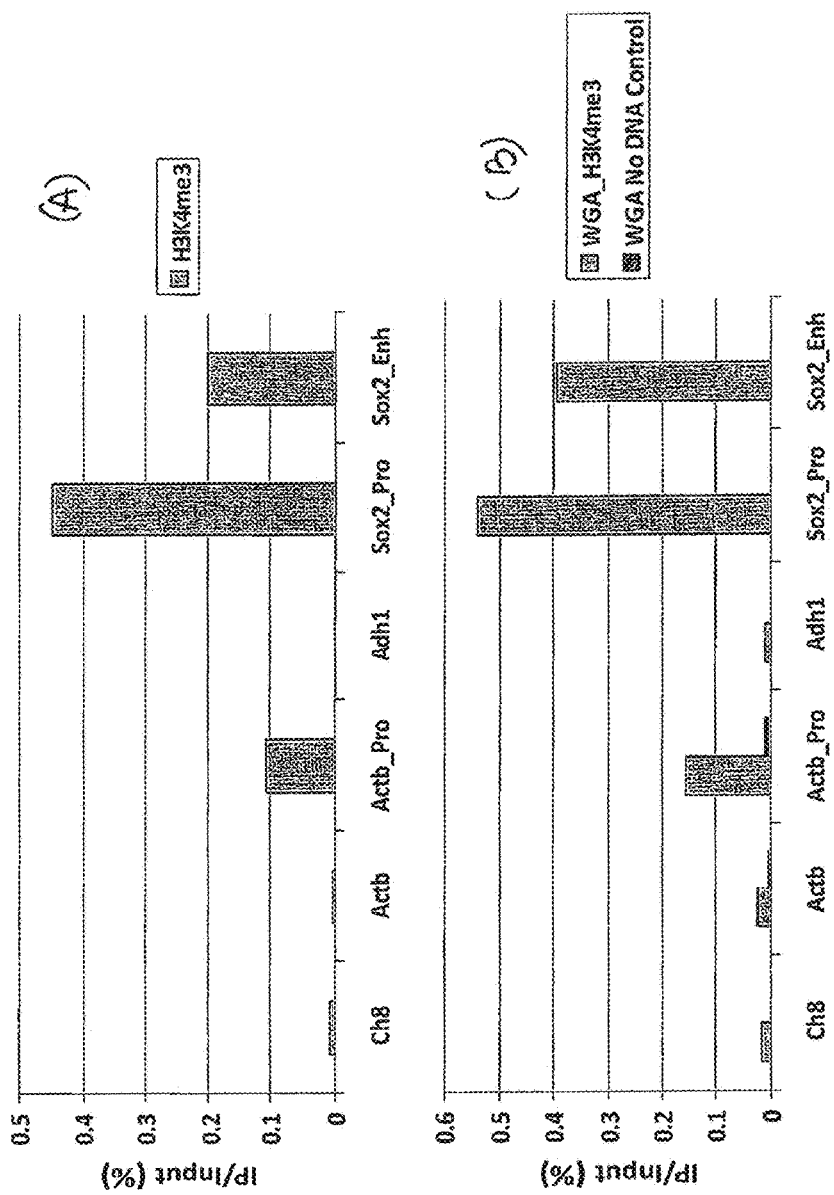
FIG. 23: Verification of WGA by Real-Time PCR
Figure 24:
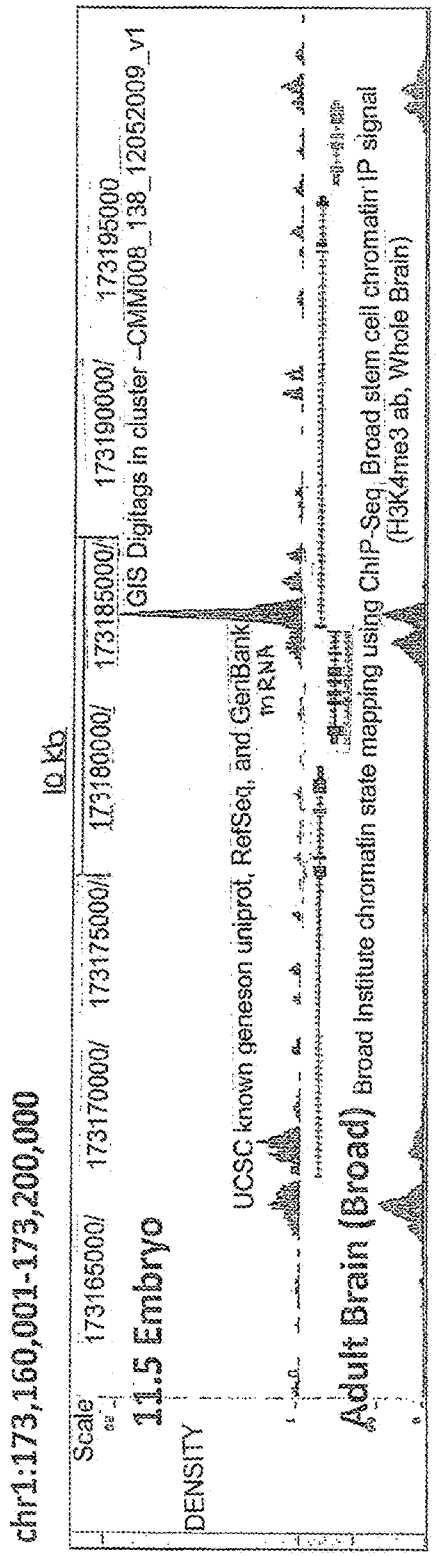
FIG. 24: 11.5 dpc Forebrain H3K4me3 ChIP-seq Results
Figure 25:
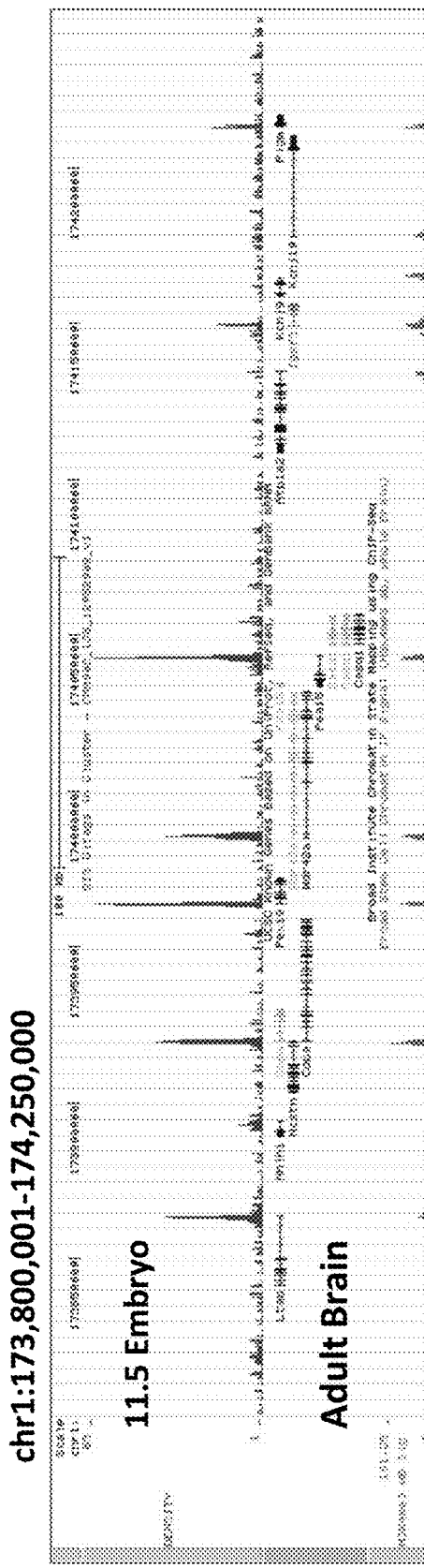
FIG. 25: (A) 11.5 dpc Forebrain ChIP-seq Results (B) ChIP DNA sample was generated using antibody against tri-methyl lysine 4 of histone H3 (H3K4me3) with mouse embryonic stem cells. Fourth row shows imput, non-enriched control sample library. Each sample was sequenced by GIS's Illumina sequencing platform and mapped and annotated by standard computational processing.
Figure 25:
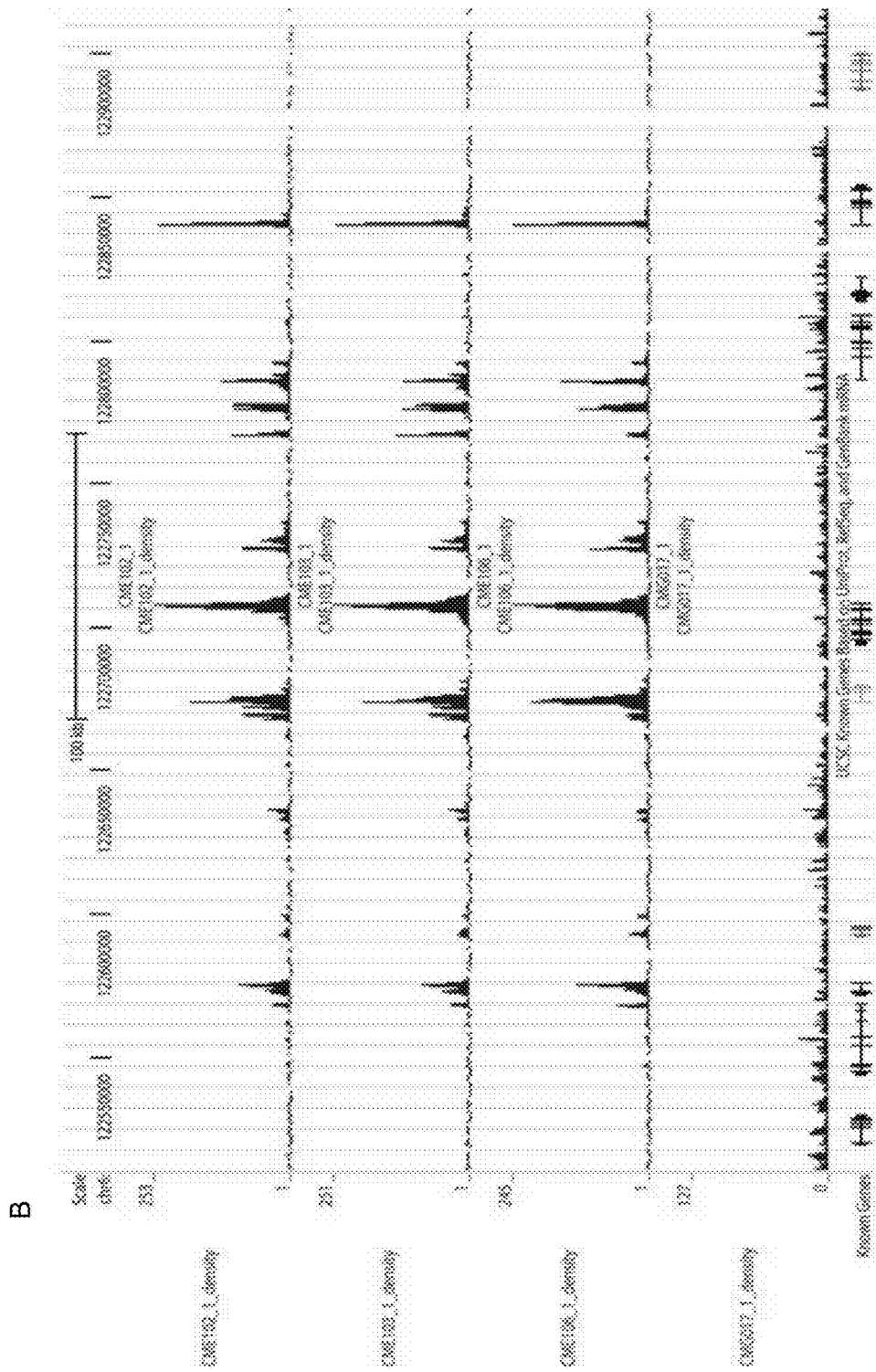

We have experimentally confirmed that this second digestion further improved mapping of sequences from amplified genomic DNA fragments (FIGS. 16, 21 and 25).

The method has the advantage of enabling application of amplified DNA samples for next-generation sequencing.

This method is useful when a limited amount of DNA samples are amplified and analyzed by massively parallel sequencing and other sequencing methods. For examples, sample preparation for comprehensive identification or sequencing of DNA in forensic, clinical (blood, tissue, skin etc.) and environmental samples (air, soil and water etc.) can be efficiently performed by combination of DOP-PCR and the DNA processing method described here.

Therefore, this method may have commercial value as it can be used with sample preparation kits. This method may also be useful for provision of sequencing services of clinical and environmental samples. Since these limited samples may not give enough amount of DNA for conventional sample preparation methods for next generation sequencing.

The method would be useful for products that include Whole Genome Amplification kits that use DOP-PCR for DNA amplification.

Bias in the DNA library representation due to the restriction enzyme used in this method can be removed computationally.

The method is effective in reducing cost and time for sequencing.

Next Generation Sequencing

Next generation sequencing comprises methods for massively parallel sequencing such as Solexa System which is based on synthesis by DNA polymerase and SOLiD System which is based on ligation and other similar sequencing methods.

Chromatin Immunoprecipitation Assay

Chromatin Immunoprecipitation (ChIP) is a method used to determine the location of DNA binding sites on the genome for a particular protein of interest, the target sequence. This technique gives a picture of the protein-DNA interactions that occur inside the nucleus of living cells or tissues. The in vivo nature of this method is in contrast to other approaches traditionally employed to answer the same questions.

The principle underpinning this assay is that DNA-binding proteins (including transcription factors and histones) in living cells can be cross-linked to the DNA that they are binding. By using an antibody that is specific to a putative DNA binding protein, it is possible to immunoprecipitate the protein-DNA complex out of cellular lysates. The crosslinking is often accomplished by applying formaldehyde to the cells (or tissue), although it is sometimes advantageous to use a more defined and consistent crosslinker such as DTBP. Following crosslinking, the cells are lysed and the DNA is broken into pieces 0.2-1 kb in length by sonication. At this point the immunoprecipitation is performed resulting in the purification of protein-DNA complexes. The purified protein-DNA complexes are then heated to reverse the formaldehyde cross-linking of the protein and DNA complexes, allowing the DNA to be separated from the proteins. The identity and quantity of the DNA fragments isolated can then be determined by PCR. The limitation of performing PCR on the isolated fragments is that one must have an idea which genomic region is being targeted in order to generate the correct PCR target primers. This limitation is very easily circumvented simply by cloning the isolated genomic DNA into a plasmid vector and then using primers that are specific to the cloning region of that vector. Alternatively, when one wants to find where the protein binds on a genome-wide scale, a DNA microarray can be used (ChIP-on-chip or ChIP-chip) allowing for the characterization of the cistrome. As well, ChIP-Sequencing has recently emerged as a new technology that can localize protein binding sites in a high-throughput, cost-effective fashion. FIG. 1 outlines a typical Chromatin Immunoprecipitation ChIP assay.

Figure 2:
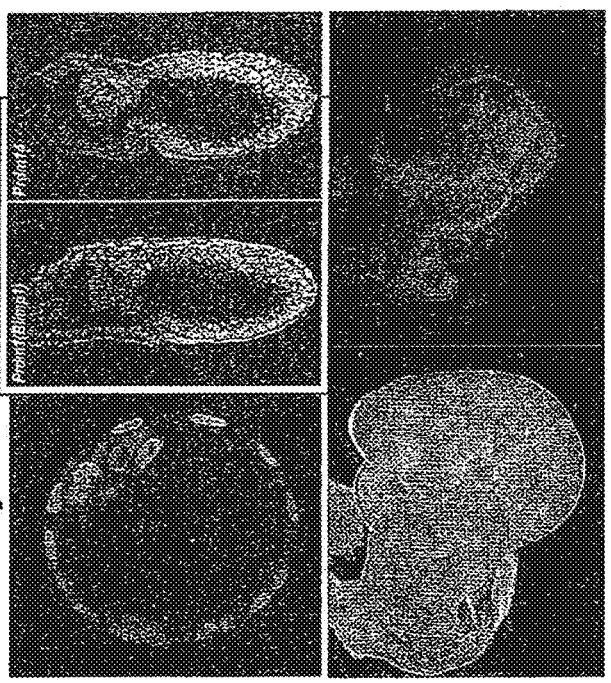
FIG. 2: ChIP assay with limited sample of, (a) Early embryo (b) Rare cell population (c) Human sample.
Figure 3:
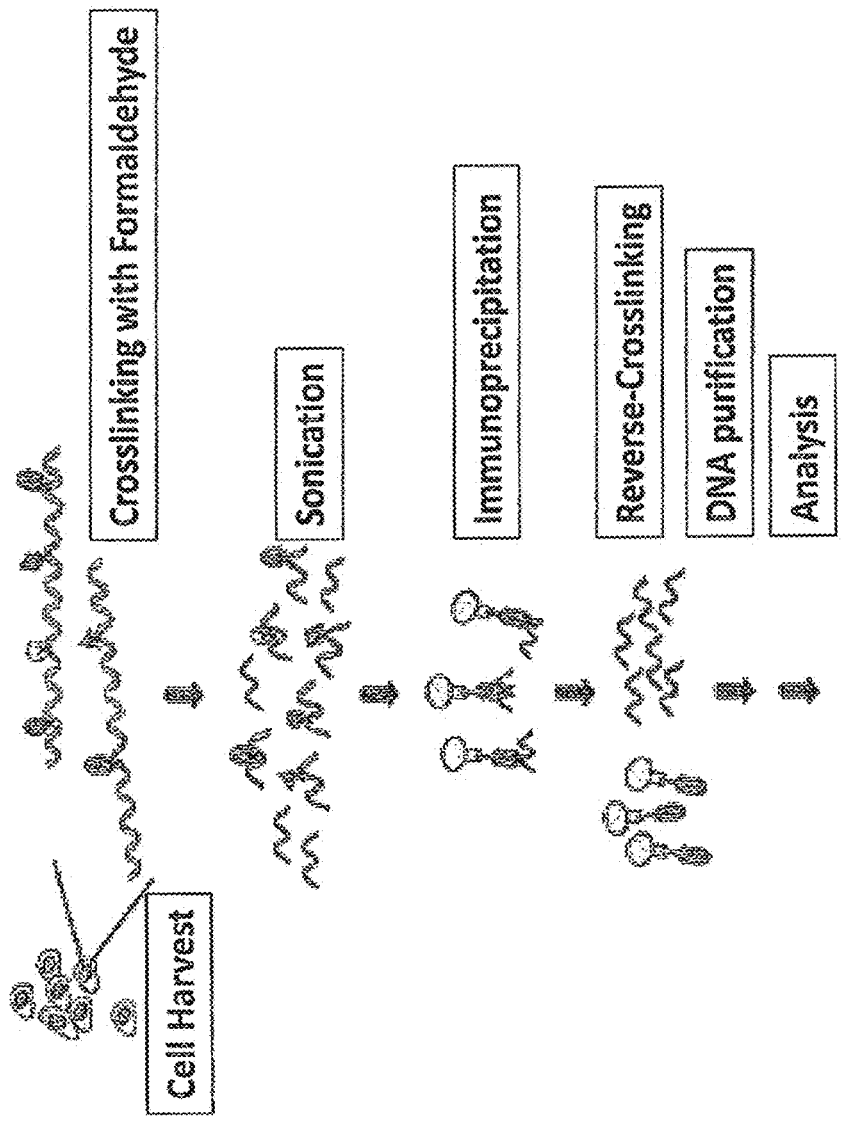
FIG. 3: Modifications on ChIP Protocol for Small-Scale Assay
Figure 4:
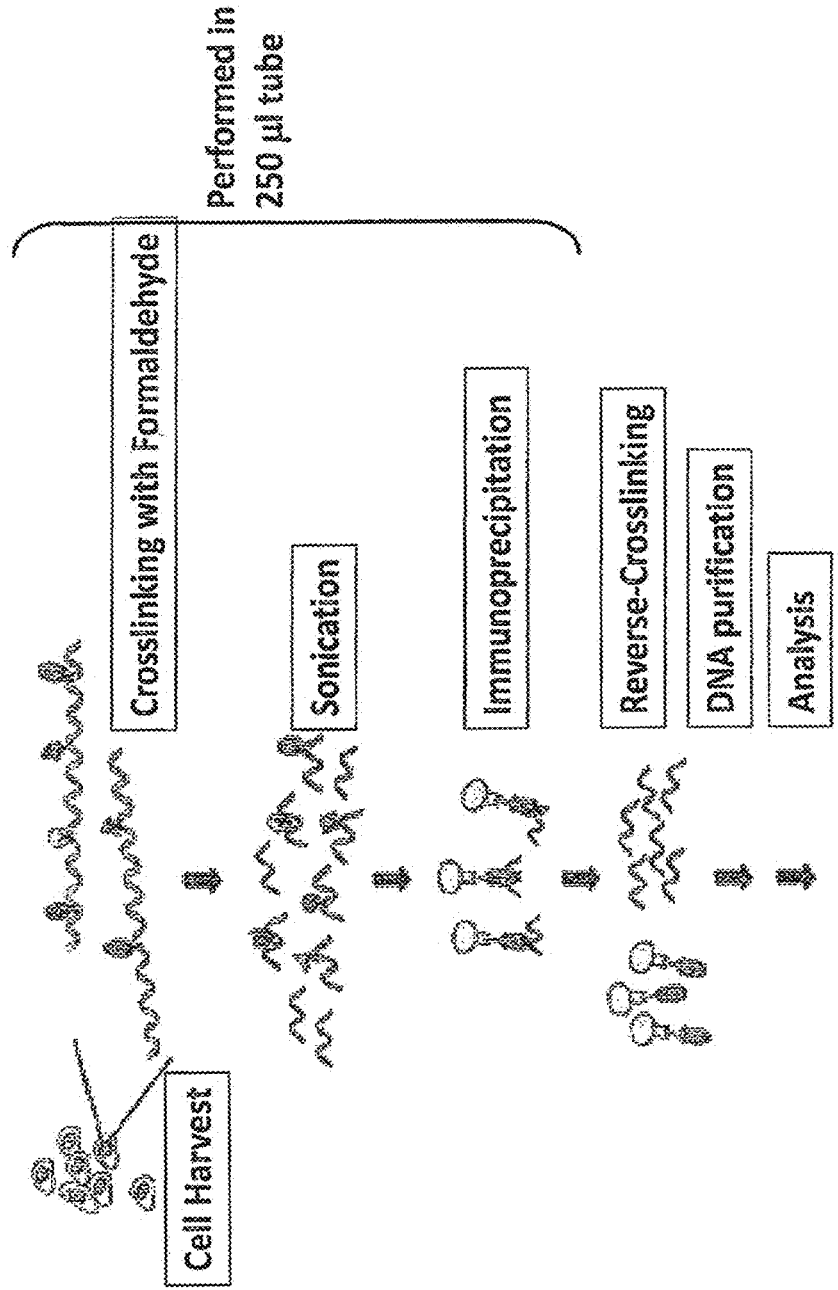
FIG. 4: Modifications on ChIP Protocol for Small-Scale Assay
Figure 5:
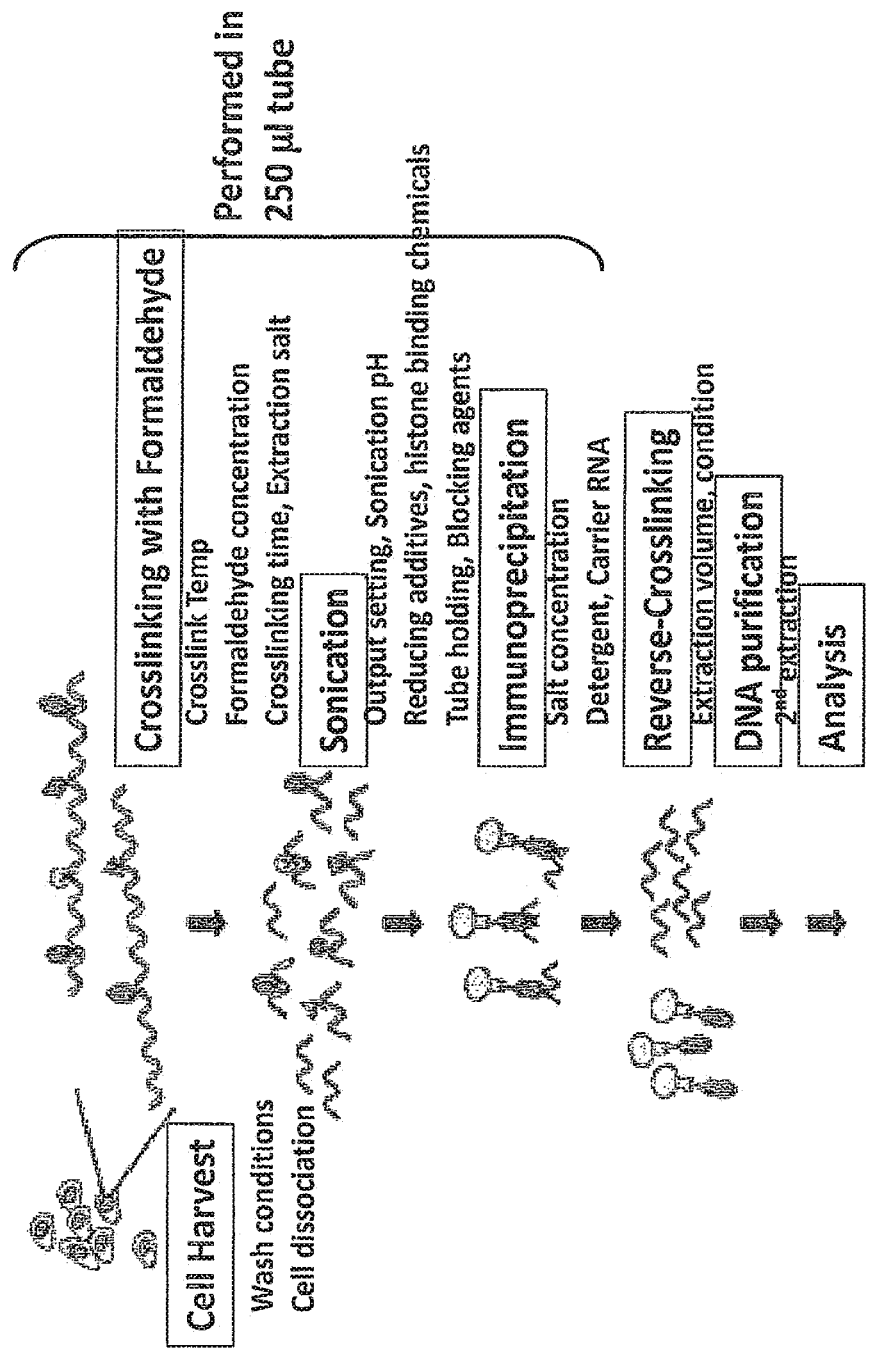
FIG. 5: Modifications on ChIP Protocol for Small-Scale Assay

This method may be modified for detection with limited sample for example in FIG. 2 using the assay outlined in FIG. 3-5.

Whole Genome Amplification

Figure 7:
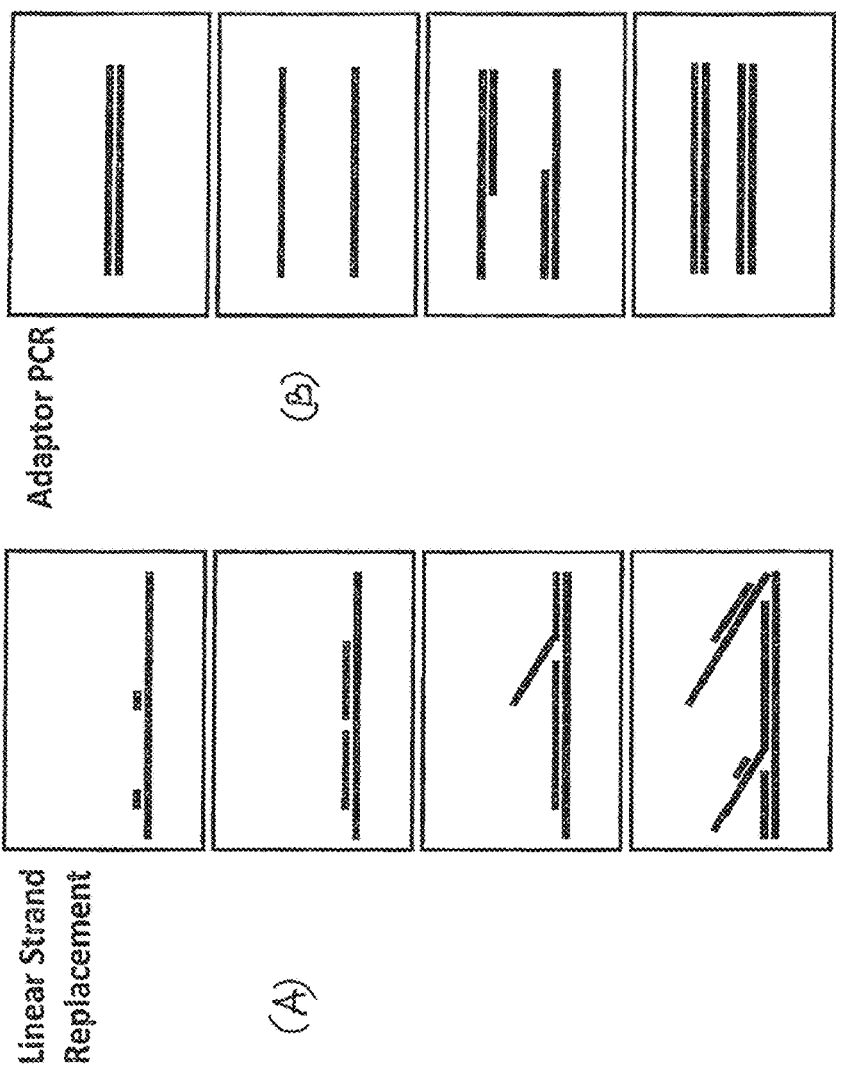
FIG. 7: Whole Genome Amplification (WGA)

Whole Genome Amplification (WGA): may be a technique designed to amplify all or some of the DNA in a sample. Several whole-genome amplification (WGA) techniques have been presented as capable of amplifying DNA from trace quantities and with less error than traditional PCR. A typical WAG protocol is described in FIG. 7. Some preferred methods to perform WGA may include multiple-displacement amplification (MDA), that uses the highly processive φ29 DNA polymerase and random exonuclease-resistant primers in an isothermal amplification reaction. This method is based on strand-displacement synthesis there are commercially available MDA kits such as GE MDA kit and the Sigma WGA kit. Other preferred methods may include PCR-based methods for WGA including degenerated oligonucleotide primed PCR (DOP-PCR) and primer extension PCR and ligation mediated PCR (LM-PCR). WGA kit (Sigma): may be a commercially available kit for conducting whole genome amplification. A new WGA method known as OmniPlex, converts randomly fragmented genomic DNA into a library of inherently amplifiable DNA fragments of defined size. This library can be effectively amplified several thousand fold with the help of a high-fidelity DNA polymerase. The library can be re-amplified to achieve a final amplification of over a million fold without degradation of representation. Similarly any WGA known in the art may be suitable for the invention.

Potential advantages of WGA include amplifying DNA from picogram amounts, and large cost and time savings compared with alternatives such as generating cell lines from individuals. Typically between 0.1 to 10 ng of starting genomic DNA can be used for WGA.

Degenerate Oligonucleotide Primed PCR (DOP-PCR)

Figure 8:
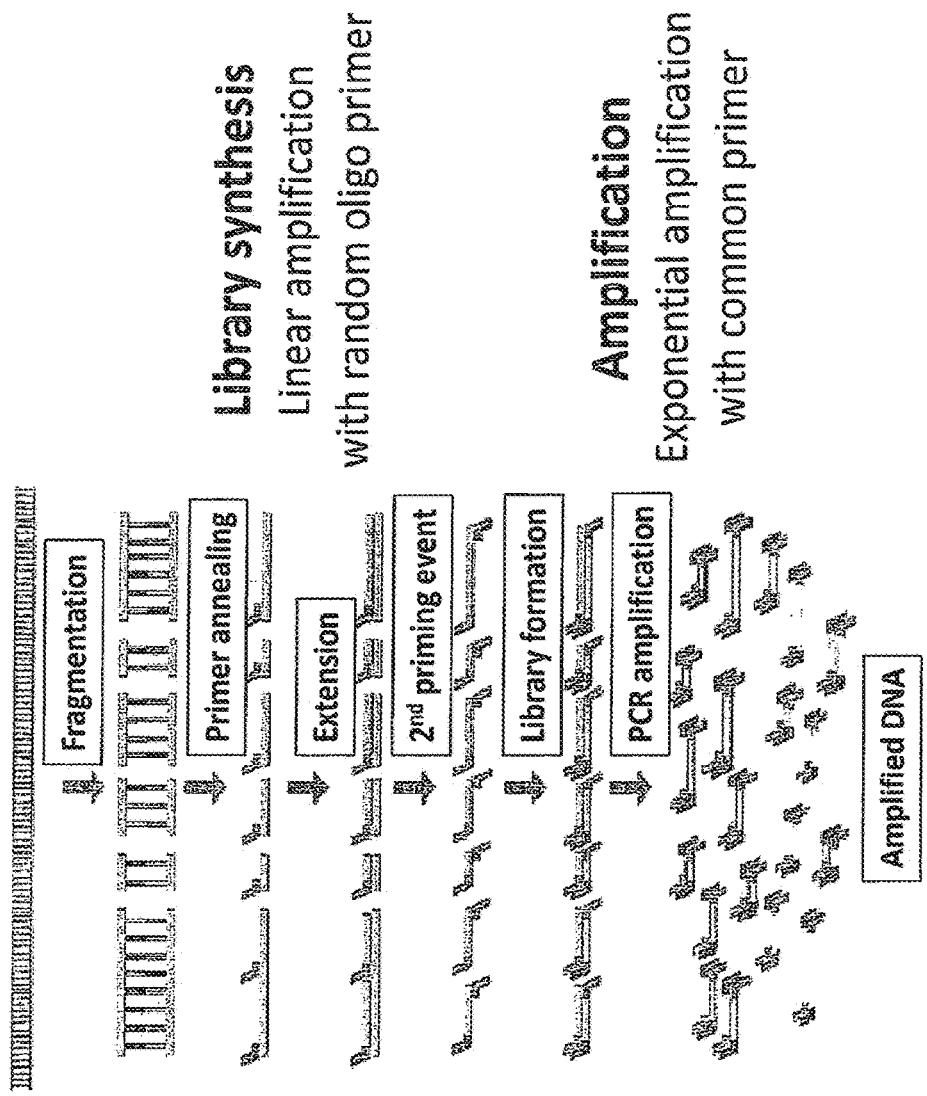
FIG. 8: Degenerate Oligonucleotide Primed-PCR (DOP-PCR)
Figure 9:
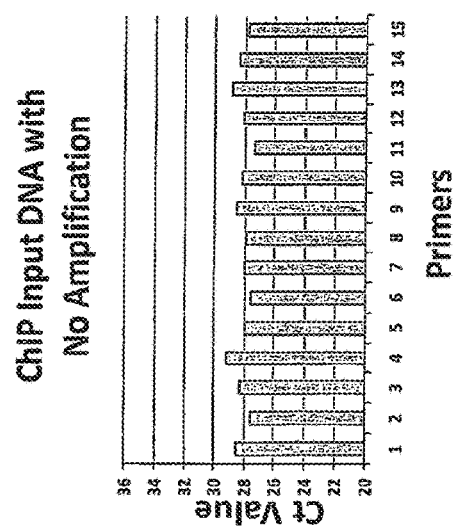
FIG. 9: WGA Test with ChIP Input DNA, ChIP Input DNA with No Amplification
Figure 10:
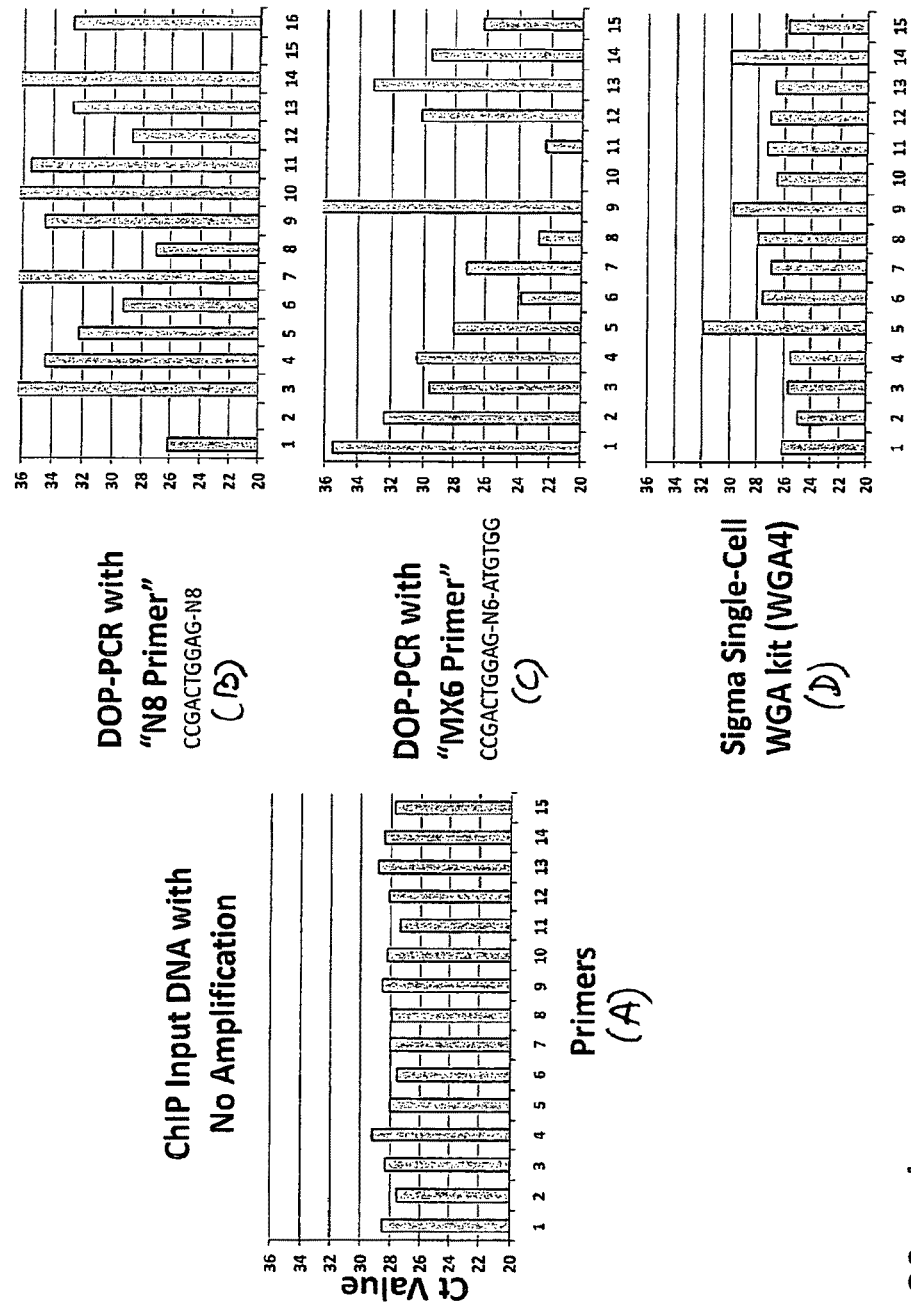
FIG. 10: WGA Test with ChIP Input DNA
Figure 11:
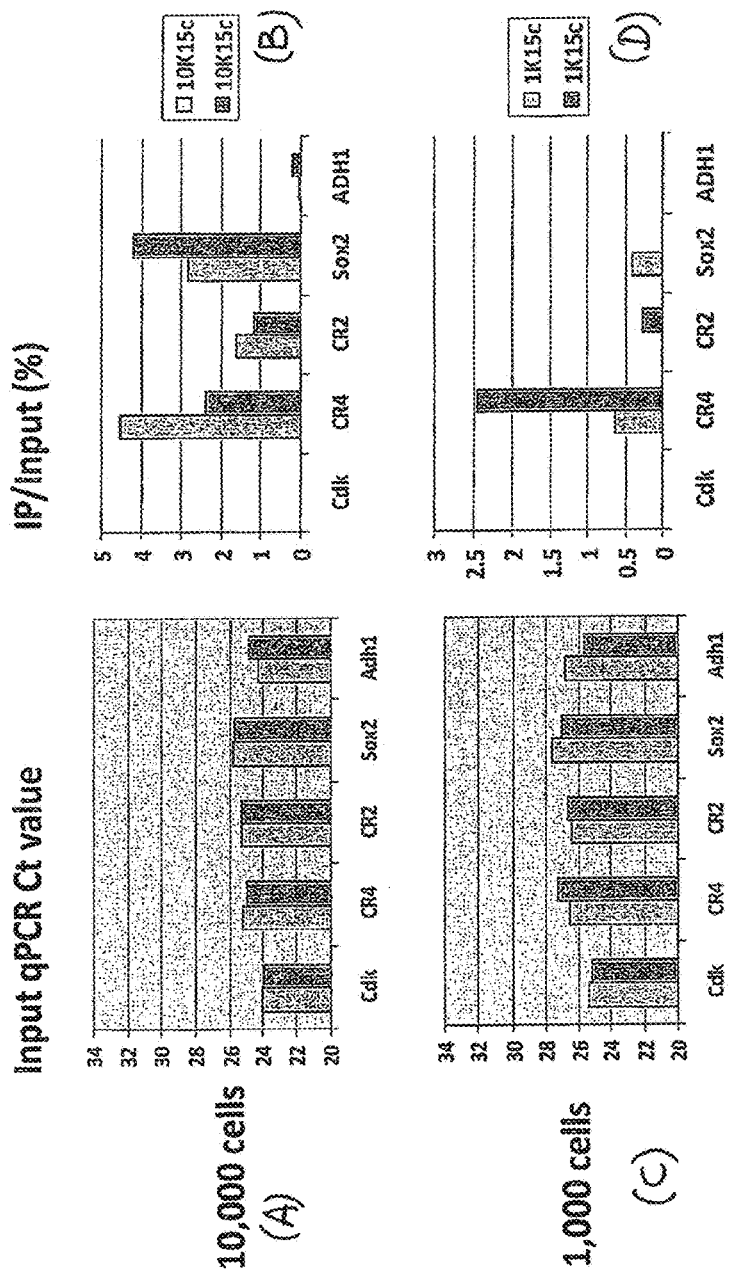
FIG. 11: Oct4 ChIP-qPCR assay with 10K and 1K mES cells
Figure 12:
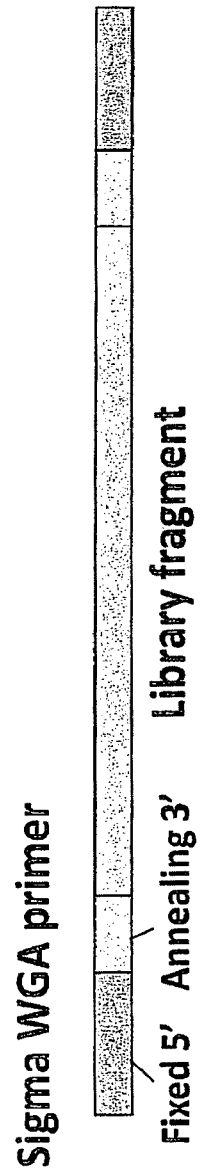
FIG. 12: Processing ChIP Material for Solexa Sequencing

The degenerate-oligonucleotide-primed PCR (DOP-PCR) method allows complete genome coverage in a single reaction. In contrast to the pairs of target-specific primer sequences used in traditional PCR, only a single primer, which has defined sequences at its 5'-end and 3'-end and a random hexamer sequence between them, is used here. DOP-PCR comprises two different cycling stages. In stage 1 (low stringency), low-temperature annealing and extension in the first five to eight cycles occurs at many binding sites in the genome. The 3'-end of the primer binds at sites in the genome complementary to the 6-bp well-defined sequence at the 3'-end of the primer (~$10^6$ sites in the human genome). The adjacent random hexamer sequence (displaying all possible combinations of the nucleotides A, G, C, and T) can then anneal and tags these sequences with the DOP primer. In stage 2 (high stringency; >25 cycles), the PCR annealing temperature is raised, which increases priming specificity during amplification of the tagged sequence. DOP-PCR generates a range of DNA fragments (200-1000 bp). FIG. 8 outlines a typical degenerate-oligonucleotide-primed PCR (DOP-PCR) method.

Nucleic Acids

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein encoding sequence that has been removed from its naturally occurring environment, and includes recombinant or cloned DNA isolates and chemically synthesized analogs or analogs biologically synthesized by heterologous systems.

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, i.e., the taget gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material, and the like by a variety of techniques such as that Known in the art. If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP may be added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 degree C. Most conveniently the reaction occurs at room temperature.

Primers

Primers of the invention comprise a primer sequence comprising a target primer sequence and a recognition site for a restriction enzyme. Preferably the restriction enzyme cleaves the sequence outside of the recognition site. Preferably the recognition site comprises SEQ ID NO.: 1.

Specific oligonucleotide primers may be derived from target gene sequence. Primers direct amplification of a target polynucleotide prior to sequencing. Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of the target extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers that may be used in diagnostic assays derived from the present invention should be designed to be substantially complementary to each strand of the taget genomic gene sequence. This means that the primers must be sufficiently complementary to hybridise with their respective strands under conditions that allow the agent for polymerisation to perform. In other words, the primers should have sufficient complementarity with the 5' and 3' sequences flanking the detection site to hybridise therewith and permit amplification of the target genomic gene sequence.

Typically, one primer will be complementary to the negative (−) strand of the taget gene sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target gene sequence. Because these newly synthesized sequences are also templates, repeated cycles of denaturing, primer annealing, and extension results in exponential production of the region defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as known in the art.

The agent for polymerisation may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (ie, those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each taget gene sequence nucleic acid strand. Generally, the synthesis will be initiated at the 3' end of each primer and proceed in the 5' direction along the template strand, until synthesis terminates, producing molecules of different lengths.

The newly synthesised target strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic gene sequence nucleic acid sequence to the extent necessary for detection. The amount of the specific nucleic acid sequence produced will accumulate in an exponential fashion.

The amplification products may be detected by Southern blot analysis, without using radioactive probes. In such a process, for example, a small sample of DNA containing a very low level of the nucleic acid sequence of the target gene sequence is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labelled, as described herein.

Sequences amplified by the methods of the invention can be further evaluated, detected, cloned, sequenced by the methods discussed above, and the like, either in solution or after binding to a solid support, by any method usually applied to the detection of a specific DNA sequence such as PCR, oligomer restriction, allele-specific oligonucleotide (ASO), probe analysis, oligonucleotide ligation assays (OLAs), and the like.

Preferably, the method of amplifying nucleic acids is by WGA, as described herein or real time PCR and as is commonly used by those of ordinary skill in the art. Alternative methods of amplification have been described and can also be employed as long as the gene sequence is amplified using primers of the invention in the alternative means. Such alternative amplification systems include but are not limited to self-sustained sequence replication, which begins with a short sequence of RNA of interest and a T7 promoter.

Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. These other methods can also be used to amplify the gene sequence as described in the method of the invention.

PREFERRED EMBODIMENTS

Example 1

Processing of Amplified Fragments to Expose Internal Part

Figure 13:
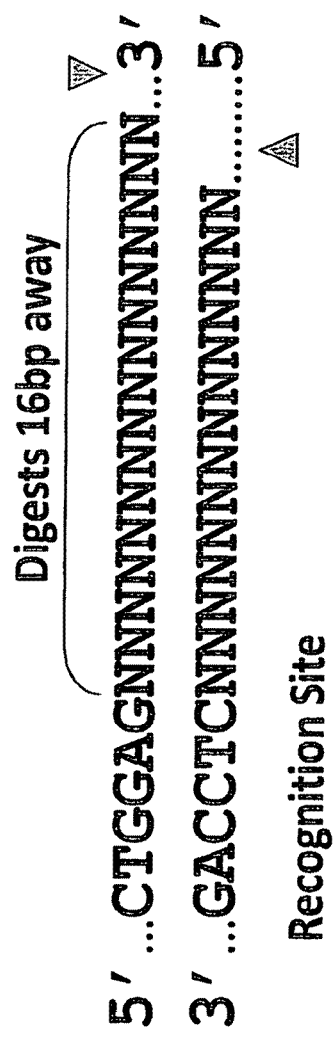
FIG. 13: Bpm I Restriction Enzyme
Figure 14:
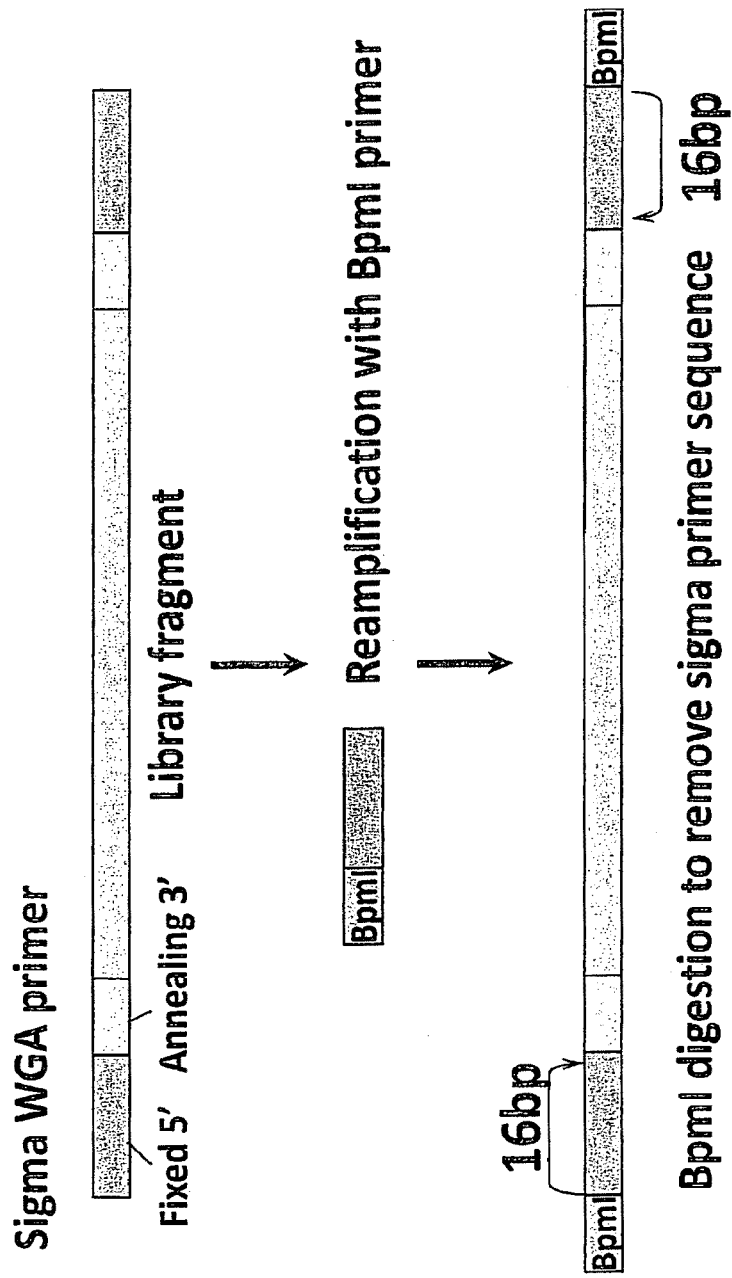
FIG. 14: Processing ChIP Material for Solexa Sequencing

This method uses BpmI or other enzymes that cleave outside of recognition site. The example of BpmI enzyme shows that this enzyme cleaves 16 base pairs away from its recognition sequence (FIG. 13).

DOP-PCR products, (FIG. 14) shows example of an, amplified product using Sigma Whole Genome Amplification Kit, are PCR amplified with primer that consists of fixed primer sequence for Whole Genome Amplification Kit (indicated with the darker colour) and BpmI site (labeled). Following amplification, the fixed primer part is trimmed by BpmI digestion.

Figure 20:
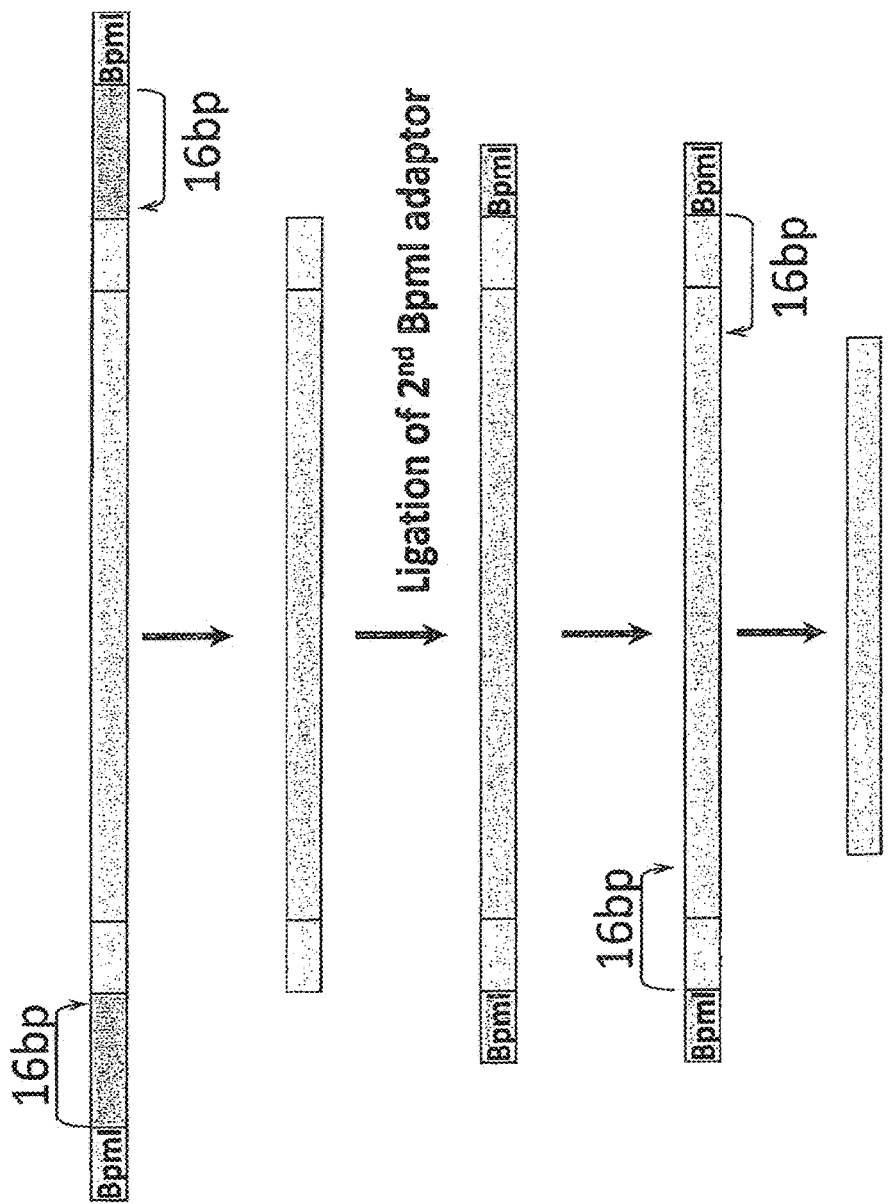
FIG. 20: $2^{nd}$ Digestion of WGA Products

If one cleavage is not sufficient for exposure of original DNA sample sequence part, a second BpmI adaptor can be ligated to dephosphorylated library. This ligation product can be digested again by a BpmI enzyme (FIG. 20).

Example 2

Improved Mapping Efficiency by Second Restriction Enzyme Digestion

Figure 26:
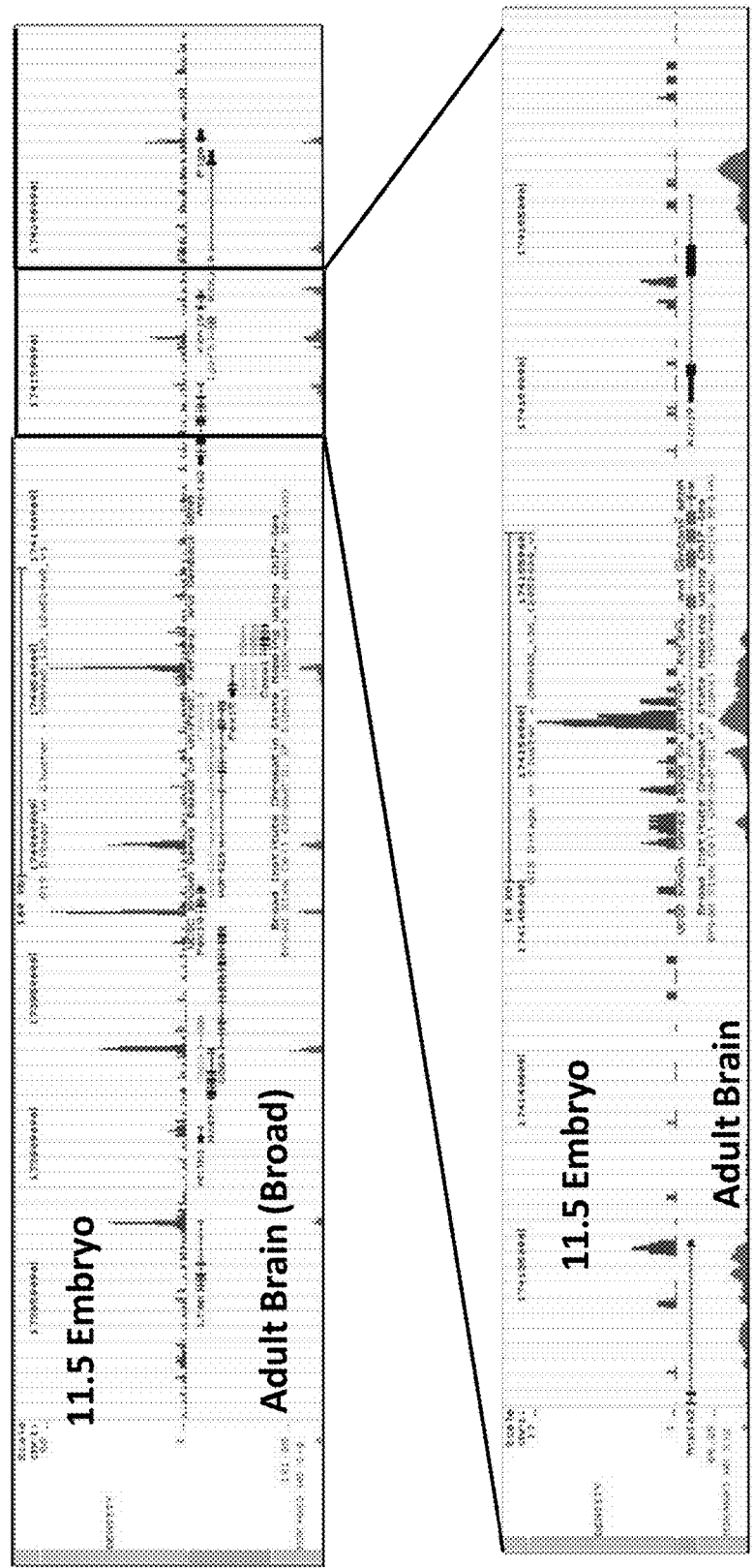
FIG. 26: 11.5 dpc Forebrain ChIP-seq Results
Figure 27:
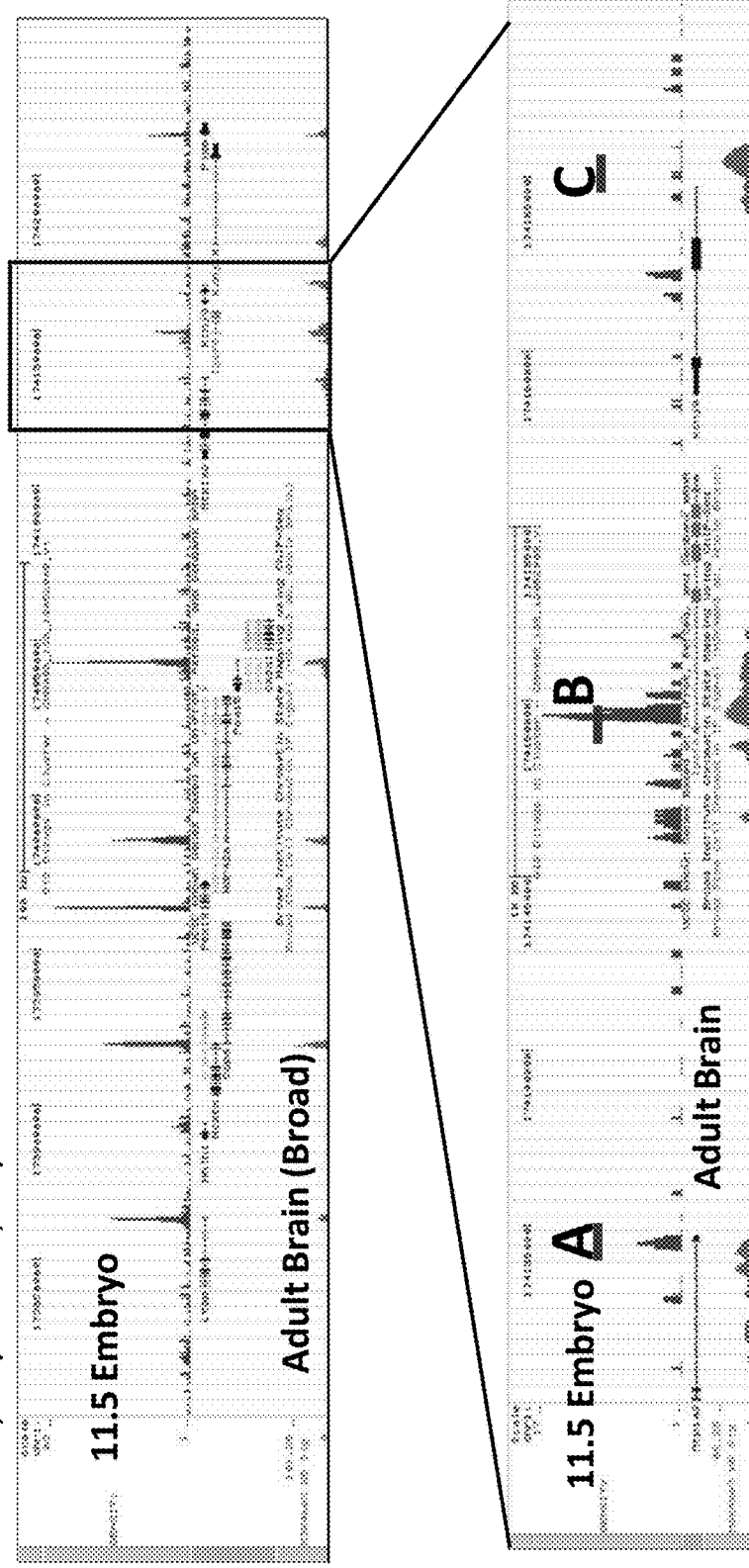
FIG. 27: 11.5 dpc Forebrain ChIP-seq Results
Figure 28:
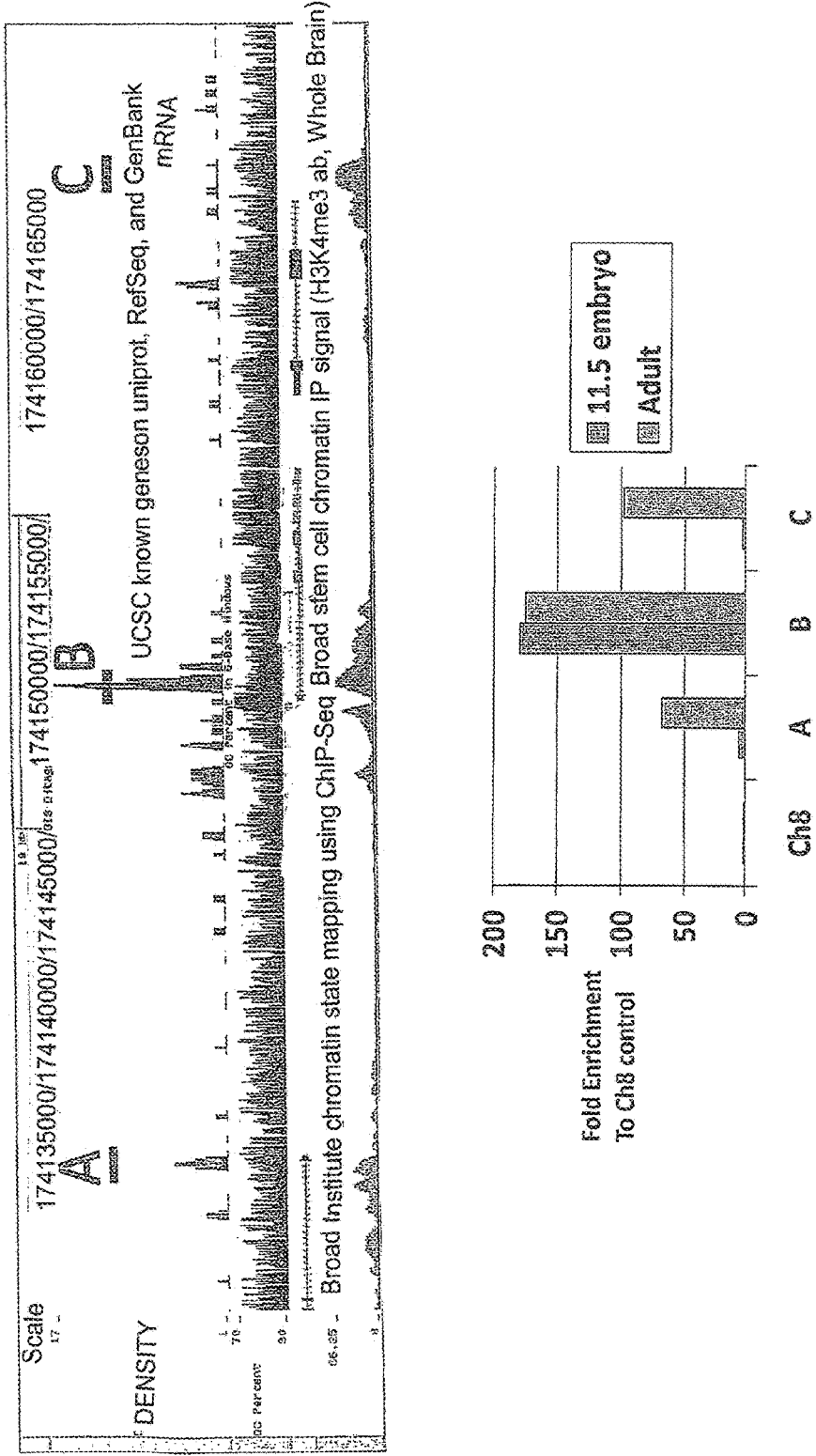
FIG. 28: Verification of ChIP-seq Results by Real-Time PCR
Figure 29:
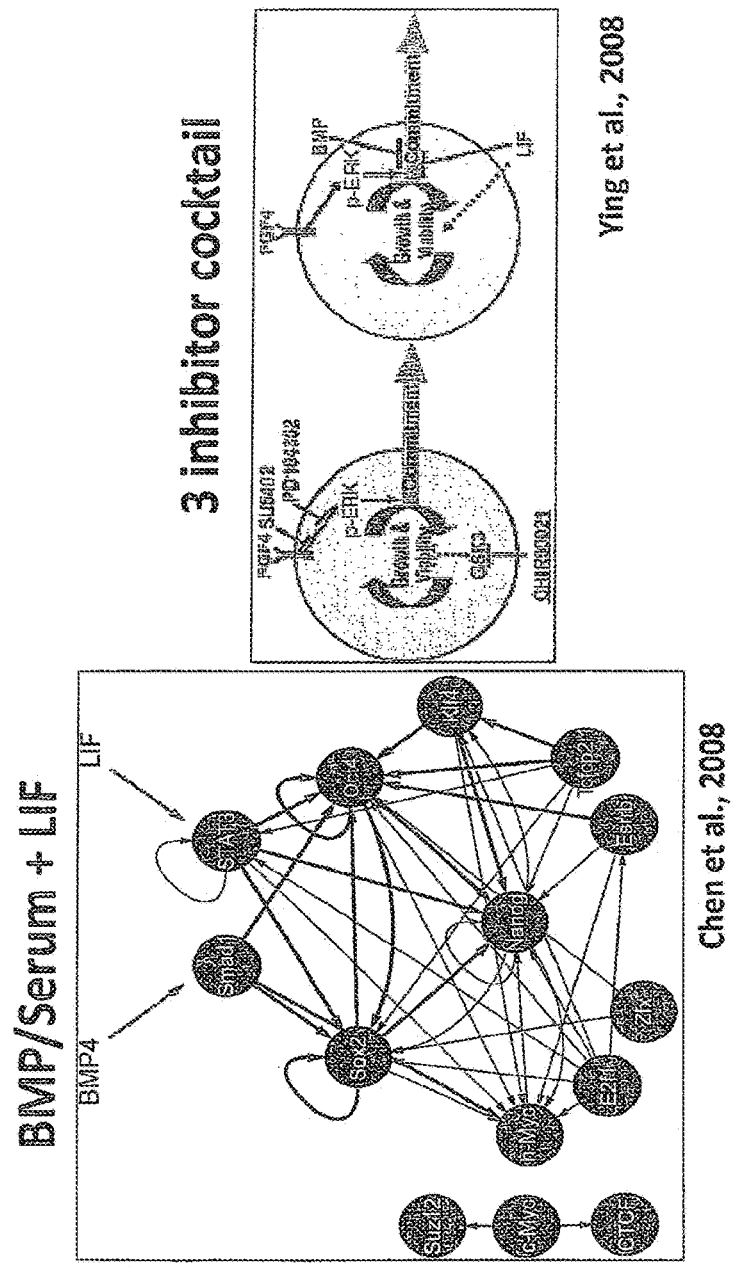
FIG. 29: Maintenance of Embryonic Stem Cells
Figure 30:
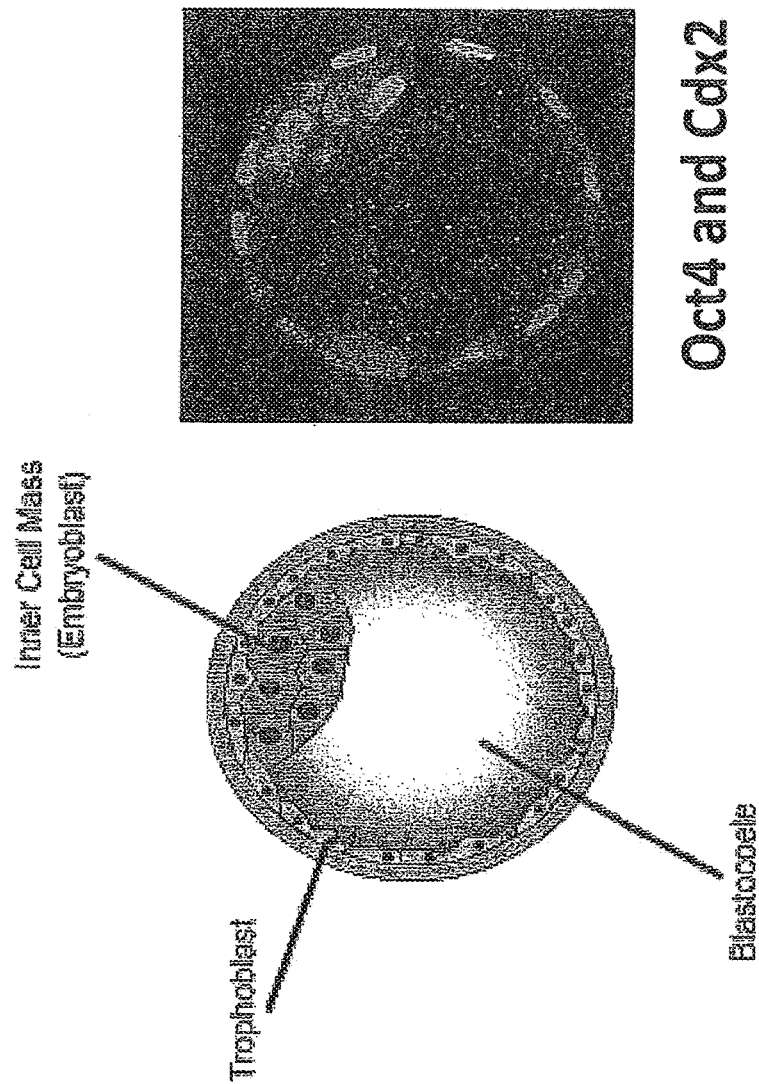
FIG. 30: Oct4 ChIP with Mouse Blastocysts
Figure 31:
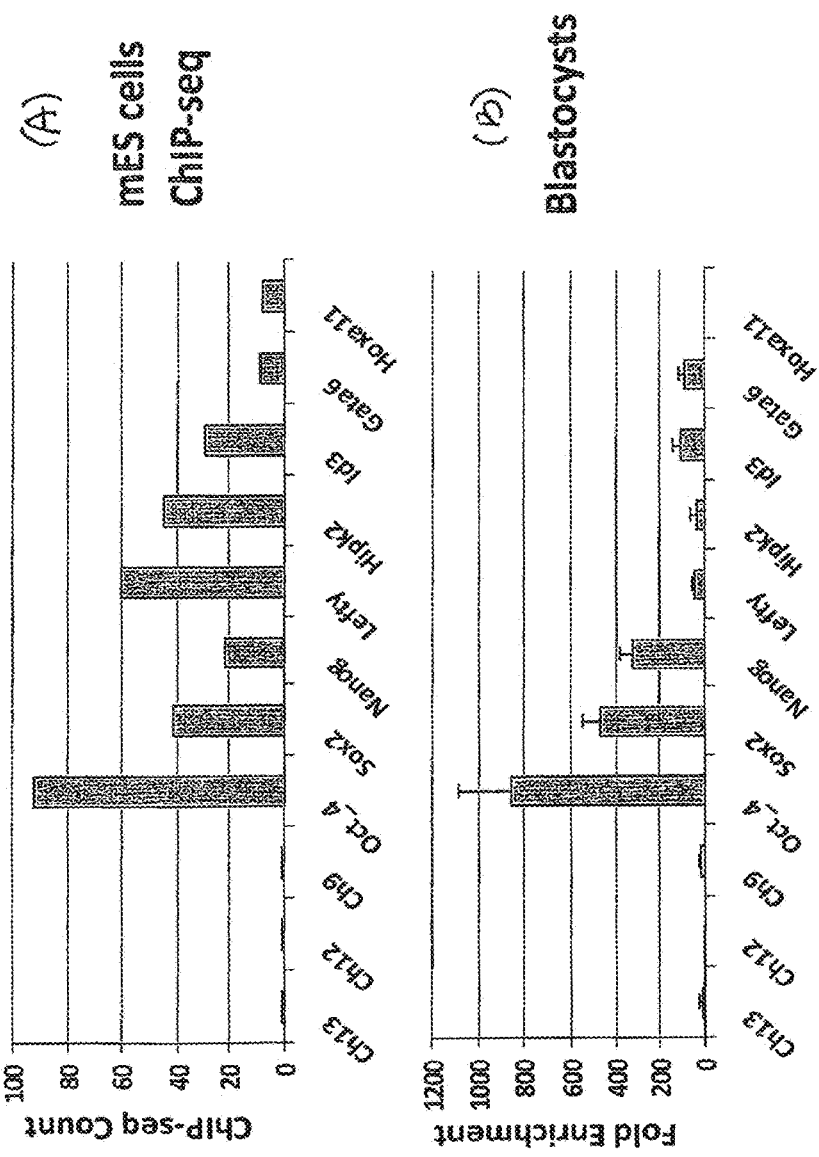
FIG. 31: Oct4 ChIP: ES Cells vs ICM
Figure 33:
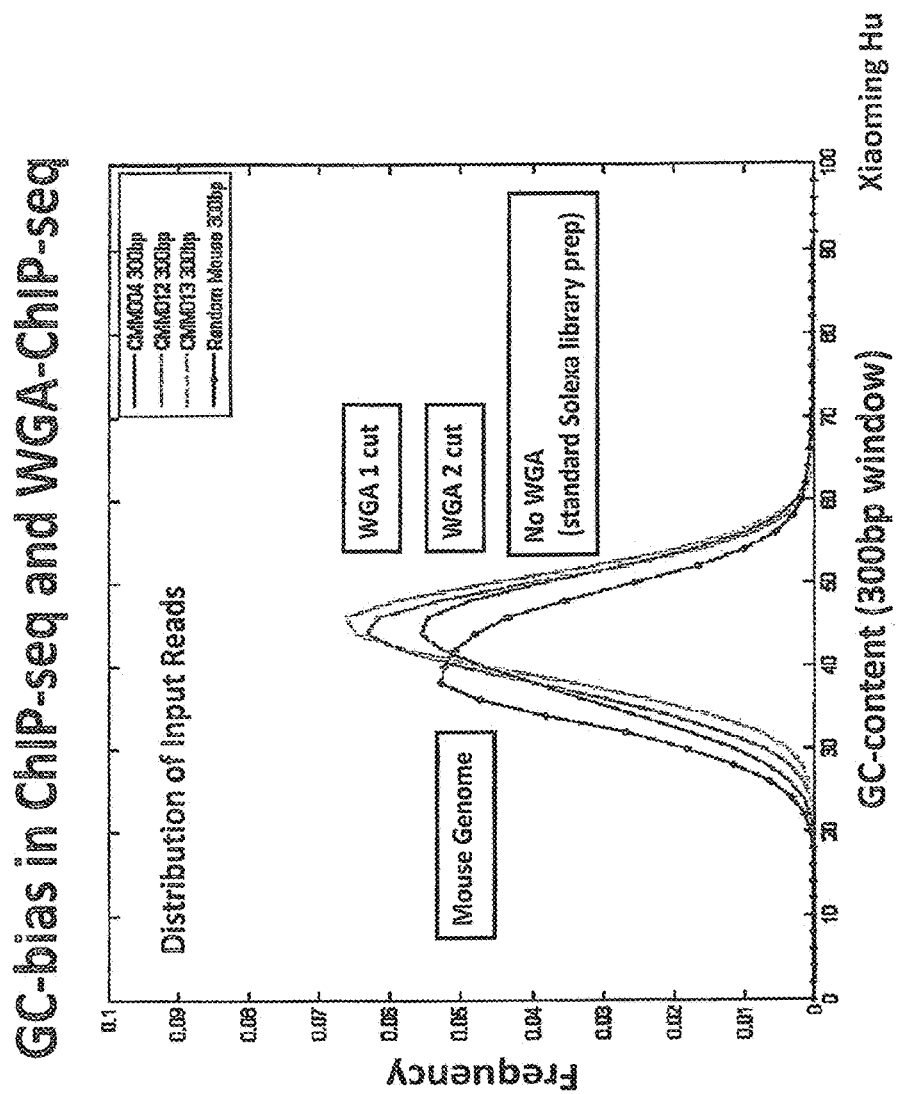
FIG. 33: GC-bias in ChIP-seq and WGA-ChIP-seq

This processing method has been successfully applied for sequencing of chromatin immunoprecipitation DNA by Illumina's platform. FIG. 21(c) shows improved mapping efficiency by second BpmI digestion in mapping of Solexa sequence reads. FIG. 21(b) also confirms reduced mapping error rate at 5' end of sequencing. This method made it possible to analyse epigenetic modification status of chromatin in developing mouse forebrain as shown in FIG. 26 (ChIP-seq view of histone H3K4me3 modification; 11.5: embryonic forebrain, and Adult Brain data from Broad Institute database as reference).

<200 molecules/locus: too little for analysis by standard method such as Real-time PCR, Microarray or Solexa sequencing hence there is a Need to amplify the ChIP DNA.

|  | Passed Filter | Mapped |
| --- | --- | --- |
| Lane 5: no WGA | 11,590,772 | 7,904,285 |
| Lane 7: WGA 8 cycles | 12,399,781 | 5,247,571 |

Figure 15:
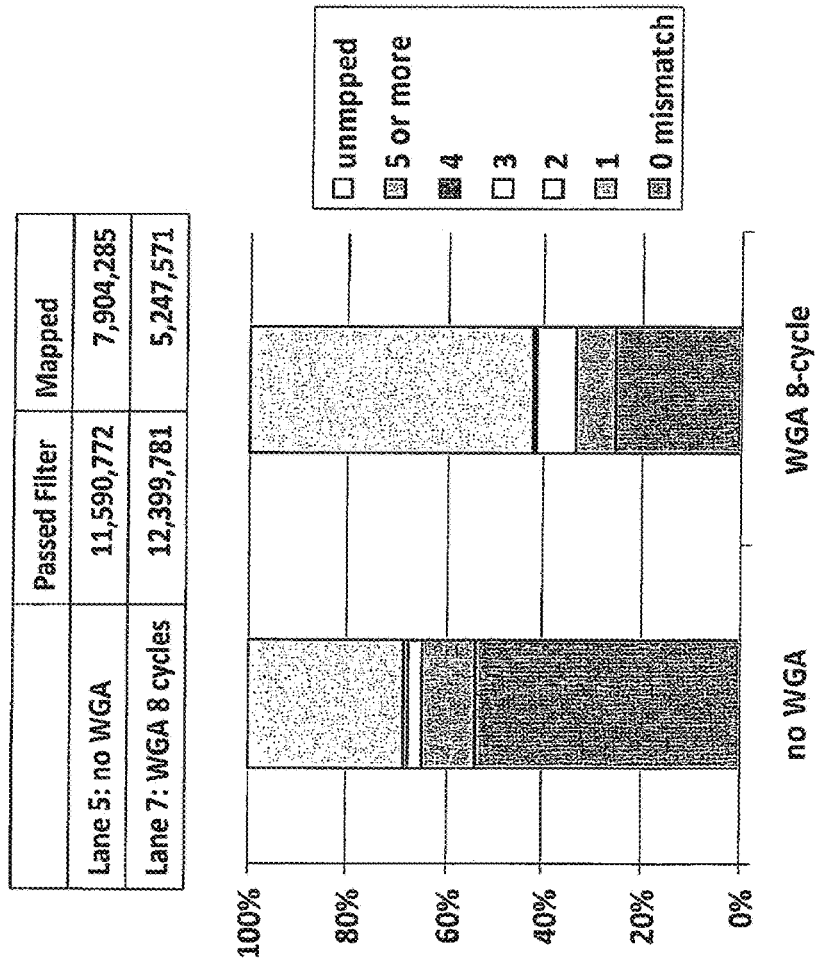
FIG. 15: Low Mapping Efficiency of WGA Library

This is further depicted in FIG. 15.

Example 3

ChIP with Mouse Embryo Forebrain 36 dissected forebrain tissue (~12 M cells), the cells are dissociated, and fixed in 1% Formaldehyde followed by ChIP Histone H3K4me3 treatment then 8-Cycle WGA (16 ng DNA obtained) and Solexa library preparation. See results depicted in FIGS. 22 to 28.

Example 4

ChIP with Mouse Blastocysts

Frozen Stock of 256 Blastocysts (Estimated ~5,000 ICM Cells) were Fixed with 1% Formaldehyde then ChIP specific to Oct4 was conducted WGA 15 cycles (Obtained ~500 ng DNA) followed by Real-time PCR. See results depicted in FIGS. 29 to 32.

Example 5

ChIP DNA sample was generated using antibody against tri-methyl lysine 4 of histone H3 (H3K4me3) with mouse embryonic stem cells (FIG. 25(b). Fourth row shows imput, non-enriched control sample library. Each sample was sequenced by GIS's Illumina sequencing platform and mapped and annotated by standard computational processing.

Chroamatin-immunoprecipitation combined with massively parallel sequencing (ChIP-seq) experiment was performed with original large-scale sample i.e.; 15 ng DNA sample, (FIG. 25(B) third row from top) and small-scale i.e.; 50 pg DNA sample, (FIG. 25(B) top two rows, as duplicate).

These data show almost identical peak pattern and magnitude between original 15 ng sample and 15-cycle amplified samples from 50 pg DNA processed by our DNA processing technology—validating successful practical application of the technology with extremely small amount of samples.

While the invention has been described with reference to specific methods and embodiments, it will be appreciated that various modifications and changes may be made without departing from the invention.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

---

---

The invention claimed is:

1. A method of trimming nucleic acid fragments for sequencing comprising the steps of:
   (a) amplifying a nucleic acid fragment with a primer comprising a sequence substantially complementary to a target sequence and a first recognition site for a restriction enzyme;
   (b) digesting the amplified nucleic acid fragment with a first restriction enzyme to remove the primer of the nucleic acid fragment thereby exposing the target sequence;
   (c) ligating the target sequence with an adaptor comprising a second recognition site for a restriction enzyme, thereby producing a ligated sequence; and
   (d) digesting the ligated sequence with a second restriction enzyme at the ligated sequence for further trimming the nucleic acid fragment for sequencing.

2. The method of claim 1 wherein the first restriction enzyme cleaves sequence outside of the first recognition site and the second restriction enzyme cleaves sequence outside of the second recognition site.

3. The method of claim 1 wherein the first or second restriction enzyme is selected from BpmI or MmeI.

4. The method of claim 1 wherein the first or second recognition sites comprise SEQ ID NO.: 1 and the first or second restriction enzyme comprises SEQ ID NO.:2.

5. The method of claim 1 further comprising the step of forming a nucleic acid library using whole genome amplification prior to step (a).

6. The method of claim 5 further comprising the step of computationally removing any bias in the nucleic acid library.

7. A method of trimming a nucleic acid comprising the steps of:
 (a) amplifying a nucleic acid with a pair of primers, wherein each primer comprises a restriction enzyme recognition site, thereby producing an amplified nucleic acid fragment;
 (b) digesting the amplified nucleic acid fragment with a restriction enzyme that recognizes the restriction enzyme recognition site of step (a), thereby producing a digested nucleic acid fragment;
 (c) ligating the digested nucleic acid fragment with a pair of adaptors, wherein each adaptor comprises a restriction enzyme recognition site, thereby producing a ligated nucleic acid fragment; and
 (d) digesting the ligated nucleic acid fragment with a restriction enzyme that recognizes the restriction enzyme recognition site, thereby producing a trimmed target nucleic acid fragment.

8. A method of trimming a nucleic acid comprising the steps of:
 (a) amplifying a nucleic acid with a pair of primers, wherein each primer comprises a restriction enzyme recognition site, thereby producing an amplified nucleic acid fragment;
 (b) digesting the amplified nucleic acid fragment with a restriction enzyme that recognizes the restriction enzyme recognition site of step (a) and cleaves nucleic acid outside of the restriction enzyme recognition site of step (a), thereby producing a digested nucleic acid fragment;
 (c) ligating the digested nucleic acid fragment with a pair of adaptors, wherein each adaptor comprises a restriction enzyme recognition site, thereby producing a ligated nucleic acid fragment; and
 (d) digesting the ligated nucleic acid fragment with a restriction enzyme that recognizes the restriction enzyme recognition site of step (c) and cleaves nucleic acid outside of the restriction enzyme recognition site of step (c), thereby producing a trimmed target nucleic acid fragment.

\* \* \* \* \*